United States Patent
Ge et al.

(10) Patent No.: US 11,931,454 B2
(45) Date of Patent: Mar. 19, 2024

(54) WET-PACKED SOFT HYDROGEL OCULAR INSERTS

(71) Applicant: Alcon Inc., Fribourg (CH)

(72) Inventors: Junhao Ge, Johns Creek, GA (US); Steve Yun Zhang, Sugar Hill, GA (US); Daqing Wu, Suwanee, GA (US); Jing Cheng, Suwanee, GA (US)

(73) Assignee: Alcon Inc., Fribourg (CH)

( * ) Notice: Subject to any disclaimer, the term of this patent is extended or adjusted under 35 U.S.C. 154(b) by 39 days.

(21) Appl. No.: 17/024,268

(22) Filed: Sep. 17, 2020

(65) Prior Publication Data

US 2021/0077385 A1    Mar. 18, 2021

Related U.S. Application Data

(60) Provisional application No. 62/901,967, filed on Sep. 18, 2019.

(51) Int. Cl.
| | | |
|---|---|---|
| *A61K 45/06* | (2006.01) | |
| *A61K 9/00* | (2006.01) | |
| *A61K 9/06* | (2006.01) | |
| *A61K 47/32* | (2006.01) | |
| *A61K 47/36* | (2006.01) | |

(52) U.S. Cl.
CPC ............ *A61K 9/0051* (2013.01); *A61K 9/06* (2013.01); *A61K 45/06* (2013.01); *A61K 47/32* (2013.01); *A61K 47/36* (2013.01)

(58) Field of Classification Search
CPC ........ A61K 9/0051; A61K 9/06; A61K 45/06; A61K 47/32; A61K 47/36
See application file for complete search history.

(56) References Cited

U.S. PATENT DOCUMENTS

| | | | |
|---|---|---|---|
| 3,961,628 A | 6/1976 | Arnold | |
| 4,281,654 A | 8/1981 | Shell | |
| 4,402,695 A | 9/1983 | Wong | |
| 4,910,015 A | 3/1990 | Sung | |
| 5,556,633 A | 9/1996 | Haddad | |
| 5,607,696 A | 3/1997 | Rivera | |
| 5,609,885 A | 3/1997 | Rivera | |
| 5,707,643 A | 1/1998 | Ogura | |
| 2004/0247681 A1 | 12/2004 | Ellis | |
| 2005/0129770 A1 | 6/2005 | Asgharian | |
| 2005/0129771 A1 | 6/2005 | Asgharian | |
| 2006/0166879 A1 | 7/2006 | Bhushan | |
| 2006/0251696 A1* | 11/2006 | Winterton | G02B 1/043 424/422 |
| 2008/0171072 A1 | 7/2008 | Burczynski | |
| 2009/0173044 A1* | 7/2009 | Linhardt | A61L 12/04 53/111 R |
| 2009/0270345 A1 | 10/2009 | Ketelson | |
| 2010/0168851 A1 | 7/2010 | Vanderbilt | |
| 2011/0059176 A1 | 3/2011 | Moro et al. | |
| 2012/0136322 A1 | 5/2012 | Alster | |
| 2012/0213840 A1 | 8/2012 | Lim | |
| 2012/0215184 A1 | 8/2012 | Lim | |
| 2013/0090612 A1 | 4/2013 | De Juan, Jr. | |
| 2015/0133878 A1 | 5/2015 | De Juan, Jr. | |
| 2016/0243219 A1 | 8/2016 | Biemans et al. | |
| 2016/0280827 A1 | 9/2016 | Anderson et al. | |
| 2016/0296532 A1 | 10/2016 | Stark et al. | |
| 2017/0056242 A1 | 3/2017 | Alster et al. | |
| 2017/0165112 A1 | 6/2017 | Stankus et al. | |
| 2017/0281408 A1 | 10/2017 | Arai et al. | |
| 2018/0161390 A1 | 6/2018 | Hsu | |
| 2018/0318239 A1 | 11/2018 | Sorgente | |
| 2019/0046434 A1 | 2/2019 | Mota Leite Machado Mariz et al. | |
| 2019/0105198 A1 | 4/2019 | Alster | |
| 2019/0142842 A1 | 5/2019 | Stark et al. | |

(Continued)

FOREIGN PATENT DOCUMENTS

| | | |
|---|---|---|
| JP | 2009296909 A | 12/2009 |
| TW | 577751 B | 3/2004 |
| WO | 9906023 A1 | 2/1999 |

(Continued)

OTHER PUBLICATIONS

Ivanov et al., Synthesis of boronate-containing copolymers of N,N-dimethylacrylamide, their interaction with poly(vinyl alcohol) and rheological behaviour of the gels, Apr. 2004, Polymer, vol. 45, pp. 2495-2505 (Year: 2004).*

Lu et al., Self-healing hydroxypropyl guar gum/poly (acrylamide-co-3-acrylamidophenyl boronic acid) composite hydrogels with yield phenomenon based on dynamic PBA ester bonds and H-bond, Oct. 28, 2018, Colloids and Surfaces A, vo. 561, pp. 325-331 (Year: 2018).*

Balasubramaniam et al., In vitro microbiological evaluation of polyvinyl alcohol-based ocular inserts of Ciprofloxacin hydrochloride, 2006, Indian J. Pharm. Sci., vol. 68 iss. 5, pp. 626-630. (Year: 2006).*

(Continued)

*Primary Examiner* — Ali Soroush
(74) *Attorney, Agent, or Firm* — Jian Zhou

(57) ABSTRACT

The invention is generally related to a soft hydrogel ocular insert that is composed of at least one hydrogel material in fully hydrated state and can be comfortable for wearing. The hydrogel material comprises polymer chains, which are derived from at least one arylborono-containing hydrophilic copolymer and at least one mucoadhesive polymer, and cyclic boronic ester crosslinks for crosslinking those mucoadhesive polymer chains and arylborono-containing hydrophilic copolymer chains to form a 3-dimensional polymer network. Those cyclic boronic ester crosslinks can be hydrolyzed slowly in the tear of the eyes of a patient, resulting in the disintegration (dissolution) of the 3-dimensional polymer network and thereby providing mucoadhesisve polymers and optionally drugs impregnated in the hydrogel ocular insert in a controlled manner.

25 Claims, No Drawings

(56) References Cited

U.S. PATENT DOCUMENTS

2019/0235277 A1* 8/2019 Zhang .................. G02C 7/049

FOREIGN PATENT DOCUMENTS

| WO | 2009064983 A1 | 5/2009 |
|---|---|---|
| WO | 2010078150 A1 | 7/2010 |
| WO | 2011037893 A2 | 3/2011 |
| WO | 2017026044 A1 | 2/2017 |
| WO | 2017035656 A1 | 3/2017 |
| WO | 2019150260 A1 | 8/2019 |
| WO | 2020100090 A1 | 5/2020 |

OTHER PUBLICATIONS

Lu et al., Self-healing hydroxypropyl guar gum/poly (acrylamide-co-3-acrylamidophenyl boronic acid) composite hydrogels with yield phenomenon based on dynamic PBA ester bonds and H-bond, Oct. 28, 2018, Colloids and Surfaces A, vol. 561, pp. 325-331. (Year: 2018).*
"Structure, Properties, and Preparation of Boronic AcidDerivatives. Overview of Their Reactions and Applications", Boronic Acids. Edited by Dennis G. Hall, Published byWiley-VCH Verlag GmbH & Co. KGaA (2005).
Anita Kumari et al: "Ocular inserts—Advancement in therapy of eye diseases", Journal of Advanced Pharmaceutical Technology & Reserch, vol. 1, No. 3, 2010, p. 291-296.
Arylboronic Acids, Sigma-Aldrich, ChemFiles 2001, 1.1, 5.
Asoh, et al., "Adhesion of poly(vinyl alcohol) hydrogels by theelectrophoretic manipulation of phenylboronicacid copolymers", J. Mater. Chem. B, 2015,3, 6740-6745.
Baeyens et al., J Control Release 52: 215-220 (1998).
Baeyens, et al., J Control Release 85: 163-168 (2002).
Ben Muirhead et al: "Phenylboronic acid based polymeric micelles for mucoadhesive anterior segment oculur drug delivery", Frontiers in Biooengineering and Biotechnology: 10th World Biomaterials Congress, Mar. 30, 2016, pp. 1-2.
Bonferoni, et al., Eur. J. Pharm. Biopharm. 57: 465-472 (2004).
Boron Compounds, Boronic acid derivatives, Tokyo Chemical Industry Co., Ltd., 2018.
Boronic Acids: Preparation and Applications in Organic Synthesis, Medicine and Materials, 2nd Edition, Edited by Dennis G. Hall, Published by Wiley-VCH Verlag GmbH & Co. KGaA (2011).
Bull, et al., "Exploiting the Reversible Covalent Bondingof Boronic Acids: Recognition, Sensing, and Assembly", Accounts of Chemical Research, 2013. vol. 46, No. 2, pp. 312-326.
Dharmendra et al., "Mucoadhesive Drug Delivery System: A Review", Int. J. Pharm. Biol. Arch. 2012, 3(6):1287-1291.
Dicolo et al., Int J Pharm 215: 101-111 (2001).
Friedrich, et al., J. Ocul. Pharmacol. Ther. 12: 5-18(1996).
Gelatt et al., Am J Vet Res 40: 702-704 (1979).
Gurtler and Gurny, Drug Dev Ind Pharm 21: 1-18 (1995).
Gurtler et al., Pharm Res 12: 1791-1795 (1995).
Hosaka et al., Biomaterials 4: 243-248 (1983).
Jennifer N. Cambre, Brent S. Sumerlin, "Biomedical applications of boronic acid polymers", Polymer 52 (2011) 4631-4643.
Joop A. Peters, "Interactions between boric acid derivatives and saccharides in aqueous media: Structures and stabilities of resulting esters", Coordination Chemistry Reviews 268 (2014) 1-22.
Karthikeyan, MB et al., Asian J. Pharmaceutics; 2008; Oct.-Dec. 192-200.
Koffler B, et al., Eye Contact Lens; 2010; 36:170-176.
LaMotte, et al., J. Am. Optom. Assoc. 56: 298-302 (1985).
Uchs, J, et al., Cornea, 2010; 29:1417-1427.
Mahe, et al., Br J Clin Pharmacol 59: 200-226 (2005).
Martinez-Aguirre, et al., "Substituent Effects and pH Profiles for Stability Constants of Arylboronic Acid Diol Esters", J. Org. Chem. 2013, 78, 4674-4684.
McDonald M, et al., Trans Am Ophthalmol. Soc., 2009; 107:214-221.
Pescina S et al., Drug Dev Ind Pharm; 2017:1472-1479.
Roy et al., "Polymers in Mucoadhesive Drug-Delivery Systems: A Brief Note", Designed Monomers and Polymers 2009, 12(6):483-495.
Sultana et al., Acta Pharma 55: 305-314 (2005).
Tomohiro Konno, Kazuhiko Ishihara, "Temporal and spatially controllable cell encapsulation using a water-soluble phospholipid polymer with phenylboronic acid moiety", Biomaterials 28 (2007) 1770-1777.
Vancoillie & Hoogenboom, Polym. Chem. 2016, 7: 5484-5495.
Wander A, and Koffler B, Ocul Surf., Jul. 2009; 7(3):154-62.
Yan Xu et al., "The biological performance of cell-containing phospholipid polymer hydrogels in bulk and microscale form", Biomaterials, vol. 3 (2010) 8839-8846.
Zahoor H. Farooqi et al., "Engineering of Phenylboronic Acid Based Glucose-Sensitive Microgels with 4-Vinylpyridine for Working at Physiological pH and Temperature", Macromol. Chem. Phys. 2011, 212, 1510-1514.
Zhen Liu and Hui He, "Synthesis and Applications of Boronate Affinity Materials: From Class Selectivity to Biomimetic Specificity", Acc. Chem. Res. 2017, 50, 2185-2193.
Zhuojun Huang et al., "Injectable dynamic covalent hydrogels ofboronic acid polymers cross-linked by bioactive plant-derived polyphenols", Biomater. Sci., 2018, 6, 2487-2495.
Ishihara, K. et al., Bioinspired Phospholipid Polymer Hydrogel System for Cellular Engineering. Macromolecular Symposia, May 21, 2015, vol. 351, No. 1, pp. 69-77.
Nakahata, M. et al., Self-Healing Materials Formed by Cross-Linked Polyrotaxanes with Reversible Bonds. Chem, Nov. 10, 2016, vol. 1, No. 5, pp. 766-775.

* cited by examiner

WET-PACKED SOFT HYDROGEL OCULAR INSERTS

This application claims the benefit under 35 USC § 119 (e) of U.S. provisional application No. 62/901,967 filed 18 Sep. 2019, incorporated by reference in its entirety.

The present disclosure generally relates to polymeric ocular insert technology, and more particularly to soft hydrogel ocular inserts that can be wet-packed for readily use and can be dissolved in eyes in a controllable manner to release lubricants and drugs into the eye (including, but not limited to the anterior and posterior segments) for an extended duration of time compared to topical drop dosage forms.

BACKGROUND

In recent years, a wide variety of research has been carried out to develop ocular inserts useful as a dosage form for treating a variety of eye disorders (see, Bonferoni, et al., Eur. J. Pharm. Biopharm. 57: 465-472 (2004); Friedrich, et al., J. Ocul. Pharmacol. Ther. 12: 5-18(1996); LaMotte, et al., J. Am. Optom. Assoc. 56: 298-302 (1985); Gelatt et al., Am J Vet Res 40: 702-704 (1979); Mahe, et al., Br J Clin Pharmacol 59: 200-226 (2005); Baeyens, et al., J Control Release 85: 163-168 (2002); Sultana et al., Acta Pharma 55: 305-314 (2005); Baeyens et al., J Control Release 52: 215-220 (1998); Dicolo et al., Int J Pharm 215: 101-111 (2001); Gurtler et al., Pharm Res 12: 1791-1795 (1995); Hosaka et al., Biomaterials 4: 243-248 (1983); Gurtler and Gurny, Drug Dev Ind Pharm 21: 1-18 (1995); Pescina, et al., Drug Dev Ind Pharm; 7:1-8 (2017); Karthikeyan, M B et al., Asian J. Pharmacol; 192-200 (2008); Luchs, J, et al., *Cornea*, 29:1417-1427 (2010); Koffler B, et al., *Eye Contact Lens;* 36:170-176 (2010); McDonald M, et al., *Trans Am Ophthalmol. Soc.*, 107:214-221 (2009); Wander A, and Koffler B, *Ocul Surf.* 7(3):154-62 (2009); and the references cited therein). Ocular inserts are usually composed of a polymeric vehicle containing the drug, have sizes and shapes designed for ophthalmic application, and are mainly used for topical therapy. These inserts are typically placed in the lower fornix conjunctiva and, less frequently, in the upper fornix conjunctiva or on the cornea. Ocular inserts can be prolonged drug release systems for effectively treating eye disorders.

There have been many attempts to construct ocular inserts for delivering a drug over a prolonged period of time, generally hours or days to perhaps months (U.S. Pat. Nos. 3,961,628, 4,281,654, 4,402,695, 4,910,015, 5,556,633, 5,607,696, 5,609,885, and 5,707,643; and U.S. Pat. Appl. Pub. Nos. 2004/0247681, 2006/0166879, 2008/0171072, 20012/0136322, 2012/0213840, 2012/0215184, 2013/0090612, 2015/0133878, 2016/0243219, 2016/0296532, 2017/0056242, 2017/0165112, 20170281408, 2018/0161390, 2018/0318239, 2019/0046434, 2019/0105198, and 2019/0142842). Ocular inserts can be divided into two general classes: non-erodible and erodible.

Non-erodible ocular inserts are usually made of matrix polymers that are not degradable or water-soluble. They can takes several forms, including, e.g., reservoir systems that are composed of a central reservoir of drug (a liquid, solid or pasty) enclosed by a semipermeable membrane; non-swellable matrix systems that consist of a solid mass comprising a liquid or solid drug dispersed or dissolved therein; or hydrogel systems that are made of water-swellable polymeric materials with drugs dispersed or dissolved therein, etc. For non-erodible ocular inserts, drug release kinetics depends mainly on the interactions between the polymer and the drug rather than in physiological conditions of the eye, thus kinetics can easily be changed by manipulating those interactions. However, the disadvantage with non-erodible ocular inserts is that they must be removed after use.

Erodible ocular inserts are usually made of matrix polymers that degrade by hydrolysis or enzymes in the tears or are simply water-soluble (dissolvable by tears). The obvious advantage of erodible ocular inserts is that it is not necessary to be removed after the functional period. However, the speed of degradation varies depending on the rate of production and removal of the tear fluid or on the concentration of enzymes, which are different for every patient. Consequently, the erodible ocular inserts are more susceptible to variations in the kinetics of drug release than the insoluble ones.

LACRISERT® inserts are commercially available erodible ocular inserts that are used to treat dry eye. LACRISERT® insert is a sterile, translucent, solid rod which measures 1.27 mm in diameter and 3.5 mm in length and is made of hydroxypropyl cellulose. For administration, it is placed into the inferior cul-de-sac of the eye beneath the base of the tarsus by a patient or a medical practitioner. Once inserted, the hydroxypropyl cellulose slowly dissolves in the eye over a period of several hours to a day. In the case of dry eye treatment, hydroxypropyl cellulose aids in tear retention by increasing tear viscosity to relieve the symptoms associated with dry eye. However, there also are challenges in using these types of inserts. For example, because LACRISERT® inserts are hard and inelastic, tend to dissolve slowly, and can remain in the eye even after 15-20 hours. The rod is hard and inelastic with edges due to rod-shaped design, there are side effects associated with use of LACRISERT® inserts, including blurred vision, foreign body sensation and/or discomfort, ocular irritation or hyperemia, hypersensitivity, photophobia, eyelid edema, and caking or drying of viscous material on eyelashes.

Despite the tremendous potential advantages of drug delivery implants, ocular inserts have not been widely used in applying drugs to the front of the eyes remains dominated by eye drops.

Therefore, there are still needs for soft ocular inserts that can be wet-packed for readily use and have controllable release of a drug for a prolonged time in eyes.

SUMMARY

In one aspect, the invention provides a soft hydrogel ocular insert which comprises a hydrogel material, wherein the hydrogel material is a crosslinked polymeric material which is a crosslinking product of at least one arylborono-containing hydrophilic copolymer including arylborono-containing repeating units each having an arylborono group and at least one mucoadhesive polymer including repeating units each having a moiety selected from the group consisting of 1,2-diol moiety, 1,3-diol moiety, α-hydroxycarboxylic acid moiety, and β-hydroxycarboxylic acid moiety, wherein said at least one arylborono-containing hydrophilic copolymer and said at least one mucoadhesive polymer are crosslinked in the crosslinked polymeric material through crosslinks each formed between one of arylborono groups of said at least one arylborono-containing hydrophilic copolymer and one 1,2-diol, 1,3-diol, α-hydroxycarboxylic acid, or β-hydroxycarboxylic acid moiety of said at least one mucoadhesive polymer.

In another aspect, the invention provides a method for producing a soft hydrogel ocular insert of the invention (as described above), comprising the steps of: curing a reactive composition in a mold to form a hydrogel which is in a form of the hydrogel ocular insert or is machined into the form of the hydrogel ocular insert, wherein the reactive composition comprises said at least one arylborono-containing hydrophilic copolymer and said at least one mucoadhesive polymer both dissolved in a water-based solvent.

In a further aspect, the invention provides a method for using of a soft hydrogel ocular insert of the invention (as described above) for treating a disease or disorder of an eye of a subject, comprising administering the hydrogel ocular insert into the eye.

DETAILED DESCRIPTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

"About" as used herein means that a number referred to as "about" comprises the recited number plus or minus 1-10% of that recited number.

"Optional" or "optionally" means that the subsequently described event or circumstance can or cannot occur, and that the description includes instances where the event or circumstance occurs and instances where it does not.

As used in this application, the term "ocular insert" refers to a sterile, thin solid or semisolid (gel) article that is placed into the cul-de-sac or conjuctival sac of an eye when being used by a patient and optionally impregnated with a drug.

As used in this application, the term "hydrogel ocular insert" refers to an ocular insert essentially made of one or more hydrogel materials.

As used in this application, the term "hydrogel" or "hydrogel material" refers to a crosslinked polymeric material which is insoluble in an aqueous solution having a pH greater than 7.4, but can hold at least 10 percent by weight of water in its three-dimensional polymer networks (i.e., polymer matrix) when it is fully hydrated in this aqueous solution.

A "vinyl-based copolymer" refers to a copolymer of at least two different vinylic monomers.

A "vinylic monomer" refers to a compound that has one sole ethylenically-unsaturated group.

The term "soluble", in reference to a compound or material in a solvent, means that the compound or material can be dissolved in the solvent to give a solution with a concentration of at least about 0.1% by weight at room temperature (i.e., from about 20° C. to about 30° C.).

The term "insoluble", in reference to a compound or material in a solvent, means that the compound or material can be dissolved in the solvent to give a solution with a concentration of less than 0.005% by weight at room temperature (as defined above).

The term "ethylenically unsaturated group" is employed herein in a broad sense and is intended to encompass any groups containing at least one >C=C<group. Exemplary ethylenically unsaturated groups include without limitation (meth)acryloyl

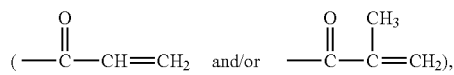

allyl, vinyl

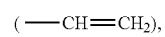

1-methylethenyl

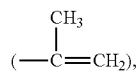

styrenyl, or the likes.

The term "(meth)acrylamide" refers to methacrylamide and/or acrylamide.

The term "(meth)acrylate" refers to methacrylate and/or acrylate.

A "hydrophilic vinylic monomer", as used herein, refers to a vinylic monomer which can be polymerized to form a homopolymer that is water-soluble or can absorb at least 10 percent by weight of water.

A "hydrophobic vinylic monomer" refers to a vinylic monomer which can be polymerized to form a homopolymer that is insoluble in water and can absorb less than 10 percent by weight of water.

An "acrylic monomer" refers to a vinylic monomer having one sole (meth)acryloyl group.

As used in this application, the term "vinylic crosslinker" refers to a compound having at least two ethylenically unsaturated groups. A "vinylic crosslinking agent" refers to a vinylic crosslinker having a molecular weight of about 700 Daltons or less.

As used in this application, the term "polymer" means a material formed by polymerizing/crosslinking one or more monomers or macromers or prepolymers.

As used in this application, the term "molecular weight" of a polymeric material (including monomeric or macromeric materials) refers to the weight-average molecular weight unless otherwise specifically noted or unless testing conditions indicate otherwise.

The term "alkyl" refers to a monovalent radical obtained by removing a hydrogen atom from a linear or branched alkane compound. An alkyl group (radical) forms one bond with one other group in an organic compound.

The term "alkylene divalent radical" or "alkylene diradical" or "alkyl diradical" interchangeably refers to a divalent radical obtained by removing one hydrogen atom from an alkyl. An alkylene divalent group forms two bonds with other groups in an organic compound.

The term "alkyl triradical" refers to a trivalent radical obtained by removing two hydrogen atoms from an alkyl. A alkyl triradical forms three bonds with other groups in an organic compound.

The term "alkoxy" or "alkoxyl" refers to a monovalent radical obtained by removing the hydrogen atom from the hydroxyl group of a linear or branched alkyl alcohol. An alkoxy group (radical) forms one bond with one other group in an organic compound.

In this application, the term "substituted" in reference to an alkyl diradical or an alkyl radical means that the alkyl diradical or the alkyl radical comprises at least one substituent which replaces one hydrogen atom of the alkyl diradical or the alkyl radical and is selected from the group consisting of hydroxy (—OH), carboxy (—COOH), —NH$_2$, sulfhydryl (—SH), $C_1$-$C_4$ alkyl, $C_1$-$C_4$ alkoxy, $C_1$-$C_4$ alkylthio (alkyl sulfide), $C_1$-$C_4$ acylamino, $C_1$-$C_4$ alkylamino, di-$C_1$-$C_4$alkylamino, halogen atom (Br or Cl), and combinations thereof.

In this application, an "arylborono-containing vinylic monomer" refers to a vinylic monomer which comprises one sole arylborono group linked to its sole ethylenically unsaturated group through one linkage.

In this application, an "arylborono" group refers to a monovalent radical of

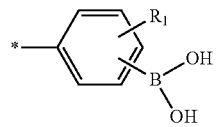

in which $R_1$ is a monovalent radical (preferably H, NO$_2$, F, Cl, Br, CF$_3$, CH$_2$OH, or CH$_2$NR$^o$R$^{o1}$ in which R$^o$ and R$^{o1}$ independent of each other are H or $C_1$-$C_4$ alkyl). It is understood that where R1 is CH$_2$OH, or CH$_2$NR$^o$R$^{o1}$, it is at the ortho-position of the boronic acid and can form intramolecular B—O or B—N coordination to lower the pKa of the boronic acid.

As used in this application, the term "phosphorylcholine" refers to a monovalent zwitterionic group of

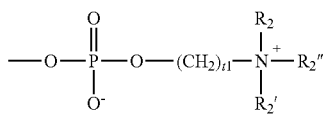

in which t1 is an integer of 1 to 5 and $R_2$, $R_2'$ and $R_2''$ independently of one another are $C_1$-$C_8$ alkyl or $C_1$-$C_8$ hydroxyalkyl.

An "initiator" refers to a chemical that can initiate free radical crosslinking/polymerizing reaction.

The term "modulus" or "elastic modulus" in reference to a contact lens or a material means the tensile modulus or Young's modulus which is a measure of the stiffness of a contact lens or a material. The modulus can be measured using a method in accordance with ANSI Z80.20 standard. A person skilled in the art knows well how to determine the elastic modulus of a silicone hydrogel material or a contact lens. For example, all commercial contact lenses have reported values of elastic modulus.

A "mucoadhesive polymer" refers to a polymer capable of bind to a mucus or mucous membrane that adheres to epithelial surfaces (e.g., the gastrointestinal tract, the lung, the eye, etc.), as known to a person skilled in the art. It should point out that mucoadhesive polymers have been widely described in the literature. See, for example, the article entitled "Mucoadhesive Drug Delivery System: A Review" by Dharmendra et al. in Int. J. Pharm. Biol. Arch. 2012, 3(6):1287-1291 and the article entitled "Polymers in Mucoadhesive Drug-Delivery Systes: A Brief Note" published by Roy et al. in Designed Monomers and Polymers 2009, 12(6):483-495.

In this application, a "6-membered acetal ring" refers to a moiety of

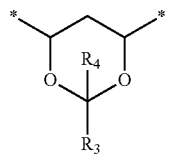

which can be formed in an acid-catalyzed reaction between a 1,3-diol moiety

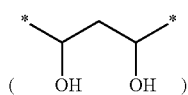

and a reactive acetal of

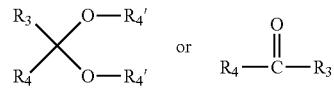

in which $R_3$ is a monovalent radical, $R_4$ is H or methyl or ethyl, and Ra' is methyl or ethyl, * represents an organic radical.

In this application, a "galactomannan polymer" refers to guar or chemically-modified guars. A "chemically-modified guar" refers to a reaction product of a guar with a reactive compound. The examples of chemically-modified guars include without limitation hydroxyethyl guar, hydroxypropyl guar (HP-guar), methyl guar, ethyl guar, propyl guar, carboxymethyl guar, carboxymethylhydroxypropyl guar, hydroxypropyltrimonium chloride guar, etc.

In general, the invention is directed to hydrogel materials suitable for making wet-packed hydrogel ocular inserts. Such hydrogel materials of the invention comprises polymer chains derived from at least one arylborono-containing hydrophilic polymer and at least one mucoadhesive polymer and cyclic boronic ester crosslinks that crosslink the polymer chains to form 3-dimensional polymer network. The hydrolysis stability of those cyclic boronic ester crosslinks depends upon the pKa of the arylborono groups forming those cyclic boronic ester crosslinks and the pH of the medium (e.g., an aqueous packaging solution or tears) in which the ocular inserts are immersed. Where the pH of the medium (e.g., an aqueous packaging solution or tears) in which the ocular inserts are immersed is lower than the pKa of the arylborono groups forming those cyclic boronic ester crosslinks, the cyclic boronic ester crosslinks are susceptible to hydrolysis. Those cyclic boronic ester crosslinks can be hydrolyzed by tears (having a neutral pH) and optionally broken by glucose in the tears in a controllable manner, thereby providing mucoadhesisve polymers and optionally drugs impregnated in the ocular insert in a controlled manner.

The invention is partly based on the discovery that such a hydrogel ocular insert can be prepared from an arylborono-containing hydrophilic copolymer including arylborono-containing repeating units each having an arylborono group having a specific pKa and a mucoadhesive polymer including repeating units each having a moiety selected from the group consisting of 1,2-diol moiety, 1,3-diol moiety, α-hydroxycarboxylic acid moiety, and β-hydroxycarboxylic acid moiety (shown in Scheme 1). The hydrolysis stability of formed cyclic boronic ester linkages (i.e., crosslinks) can be tuned to be stable in a packaging solution having an ophthalmically compatible pH (e.g., from about 7.5 to about 9.0) under autoclave conditions by selecting the arylborono groups of the arylborono-containing hydrophilic copolymer based on a desired pKa and thereby the hydrogel ocular insert is stably in fully hydrated state in an aqueous packaging solution and soft for providing the wearing comfort to a patient. It is further discovered that by varying the contents of the repeating units each having an arylborono group (i.e., varying density of cyclic boronic ester crosslinks) and/or by selectively incorporating arylborono groups having a desired pKa so as to have desired affinities toward a moiety of 1,2-diol, 1,3-diol, α-hydroxycarboxylic acid or β-hydroxycarboxylic acid (i.e., hydrolysis stability of the crosslinks) around the neutral pH of the tear fluids, one can control the rate of hydrolysis of the ocular insert in the eye.

Scheme I

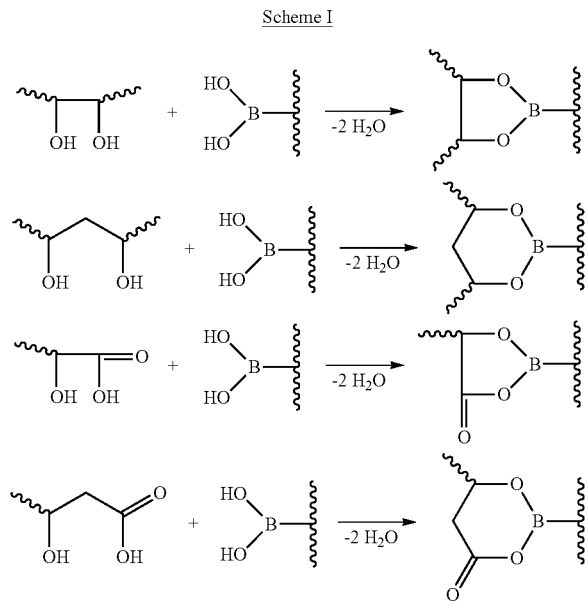

In one aspect, the invention provides a hydrogel ocular insert which comprises a hydrogel material, wherein the hydrogel material is a crosslinked polymeric material which is a crosslinking product of at least one arylborono-containing hydrophilic copolymer including arylborono-containing repeating units each having an arylborono group and at least one mucoadhesive polymer including repeating units each having a moiety selected from the group consisting of 1,2-diol moiety, 1,3-diol moiety, α-hydroxycarboxylic acid moiety, and β-hydroxycarboxylic acid moiety, wherein said at least one arylborono-containing hydrophilic copolymer and said at least one mucoadhesive polymer are crosslinked in the crosslinked polymeric material through crosslinks each formed between one of arylborono groups of said at least one arylborono-containing hydrophilic copolymer and one 1,2-diol, 1,3-diol, α-hydroxycarboxylic acid, or β-hydroxycarboxylic acid moiety of said at least one mucoadhesive polymer.

In accordance with the invention, an arylborono-containing hydrophilic copolymer can be a linear or branched polymer, so long as it can be dissolved in water. It can be an arylborono-modified hydrophilic polymer or preferably an arylborono-containing vinyl-based copolymer of an arylborono-containing vinylic monomer and at least one hydrophilic vinylic monomer.

An "arylborono-modified hydrophilic copolymer" refers to a copolymer that is obtained by reacting a phenylboronic acid compound having a first reactive functional group and a preformed hydrophilic polymer having repeating units each having a second reactive functional group which can react with one first reactive functional group in the presence or absence of a coupling agent to form a covalent linkage according to any known coupling reaction mechanism, wherein the first and second reactive functional groups independent of each other are selected from the group consisting of hydroxyl group (—OH), carboxyl group (—COOH), acid halide group, —NH$_2$, C$_1$-C$_4$ alkylamino group, epoxy group, aldehyde group, isocyanato group, azlactone group, azidirine group, and thiol group.

A persons killed in the art knows well coupling reactions between two reactive functional groups in the presence or absence of a coupling agent to form covalent bonds or linkages under various reaction conditions well known to a person skilled in the art, such as, for example, oxidation-reduction conditions, dehydration condensation conditions, addition conditions, substitution (or displacement) conditions, Diels-Alder reaction conditions, cationic crosslinking conditions, ring-opening conditions, epoxy hardening conditions, and combinations thereof.

Non-limiting examples of coupling reactions under various reaction conditions between a pair of matching co-reactive functional groups selected from the group preferably consisting of amino group (—NHR$^o$ in which R$^o$ is H or C$_1$-C$_4$ alkyl), hydroxyl group, carboxyl group, acid halide group (—COX, X=Cl, Br, or I), acid anhydrate group, aldehyde group, azlactone group, isocyanate group, epoxy group, aziridine group, and thiol group, are given below for illustrative purposes. An amino group reacts with acetal group (e.g., aldehyde or acetyl group) to form a Schiff base which may further be reduced; an amino group NHR$^o$ reacts with an acid chloride or bromide group or with an acid anhydride group to form an amide linkage (—CO—NR$^o$—); an amino group NHR$^o$ reacts with a N-hydroxysuccinimide ester group to form an amide linkage; an amino group NHR$^o$ reacts with a carboxylic acid group in the presence of a coupling agent carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl)carbodiimide, diisopropyl carbodiimide, or mixtures thereof) and N-hydroxysuccinimide to form an amide linkage; an amino group —NHR$^o$ reacts (ring-opening) with an azlactone group to form an alkylene-diamido linkage (—C(O)NH-alkylene-C(O)NR$^o$— with R$^o$ as defined above); an amino group NHR$^o$ reacts with an isocyanate group to form a urea linkage (—NR$^o$—C(O)—NH— with R$^o$ as defined above); an amino group NHR$^o$ reacts with an epoxy or aziridine group to form an amine bond (—C—NR$^o$— with R$^o$ as defined above); a hydroxyl reacts with an isocyanate to form a urethane linkage; a hydroxyl reacts with an epoxy or aziridine to form an ether linkage (—O—); a hydroxyl reacts with an acid chloride or bromide group or with an acid anhydride group to form an ester linkage; an hydroxyl group reacts with an azlactone group in the presence of a catalyst to form an amidoalkylene-carboxy linkage (—C(O)NH-alkylene-C(O)—O—); a carboxyl group reacts with an epoxy group to form an ester bond; a thiol group (—SH) reacts with an isocyanate to form a thiocarbamate linkage (—N—C(O)—S—); a thiol group reacts with an epoxy or aziridine to form a thioether linkage (—S—); a thiol group reacts with an acid chloride or bromide group or with an acid anhydride group to form a thioester linkage; a thiol group reacts with an azlactone group in the presence of a catalyst to form a linkage (—C(O)NH—C($^3$R$^4$R)—(CH$_2$)$_p$—C(O)—S—); and a thiol group reacts with a vinyl group based on thiol-ene reaction under thiol-ene reaction conditions to form a thioether linkage (—S—).

It is also understood that coupling agents with two reactive functional groups may be used in the coupling reactions. A coupling agent having two reactive functional groups can be a diisocyanate, a di-acid halide, a di-carboxylic acid compound, a di-acid halide compound, a di-azlactone compound, a di-epoxy compound, a diamine, or a diol. A person skilled in the art knows well to select a coupling reaction (e.g., anyone described above in this application) and conditions thereof to prepare a polysiloxane terminated with one or more ethylenically unsaturated groups. For example, a diisocyanate, di-acid halide, di-carboxylic acid, di-azlactone, or di-epoxy compound can be used in the coupling of two hydroxyl, two amino groups, two carboxyl groups, two epoxy groups, or combination thereof; a diamine or dihydroxyl compound can be used in the coupling of two isocyanate, epoxy, aziridine, carboxylic acid, acid halide or azlactone groups or combinations thereof.

Any phenylboronic acid compounds can be used in the preparation of arylborono-modified hydrophilic polymer, so long as they each have a reactive functional group selected from the group consisting of hydroxyl group (—OH), carboxyl group (—COOH), acid halide group, —NH$_2$, $C_1$-$C_4$ alkylamino group, epoxy group, aldehyde group, isocyanato group, azlactone group, azidirine group, and thiol group. Such phenylboronic acid compounds can be obtained from commercial sources (e.g., Sigma-Aldrich, Tokyo Chemical Industry Co., Ltd. Etc.) or be prepared according to known methods (e.g., see, Boronic Acids: Preparation and Applications in Organic Synthesis, Medicine and Materials, 2nd Edition, Edited by Dennis G. Hall, Published by Wiley-VCH Verlag GmbH & Co. KGaA (2011).

Any preformed hydrophilic polymers can be used in the preparation of arylborono-modified hydrophilic polymer, so long as they each comprise repeating monomeric units each having a reactive functional group selected from the group consisting of hydroxyl group (—OH), carboxyl group (—COOH), acid halide group, —NH$_2$, $C_1$-$C_4$ alkylamino group, epoxy group, aldehyde group, isocyanato group, azlactone group, azidirine group, and thiol group. Preferably, a hydrophilic polymer is a homo- or copolymer of a vinylic monomer selected from the group consisting of $C_2$-$C_4$-hydroxyalkyl (meth)acrylate, $C_2$-$C_4$-hydroxyalkyl (meth)acrylamide, allylalcohol, allylamine, vinylamine, amino-$C_2$-$C_4$-hydroxyalkyl (meth)acrylate, amino-$C_2$-$C_4$-hydroxyalkyl (meth)acrylamide, $C_1$-$C_3$ alkylamino-$C_2$-$C_4$ alkyl (meth)acrylate, $C_1$-$C_3$ alkylamino-$C_2$-$C_4$ alkyl (meth)acrylamide, glycerol (meth)acrylate, N-(2,3-dihydroxypropyl) (meth)acrylamide, N,N-bis(2-hydroxyethyl) (meth)acrylamide, N-tris(hydroxymethyl)methyl (meth)acrylamide, (meth)acrylic acid halide (chloride, bromide, or iodide), (meth)acrylic anhydride, maleic anhydride, acrylic acid, and $C_1$-$C_4$ alkylacrylic acid (e.g., methacrylic ethylacrylic acid, propylacrylic acid, butylacrylic acid), 2-acrylamidoglycolic acid, 3-acrylamidopropionic acid, 4-acrylamidobutanoic acid, 5-acrylamidopentanoic acid, 3-acryloyloxypropanoic acid, 4-acryloyloxybutanoic acid, 5-acryloyloxypentanoic acid, an epoxy-containing vinylic monomer (e.g., glycidyl (meth)acrylamide, hydroxyethyl (meth)acrylamide glycidyl ether, 3-hydroxypropyl (meth)acrylamide glycidyl ether, 4-hydroxybutyl (meth)acrylamide glycidyl ether, glycidyl (meth)acrylate, hydroxyethyl (meth)acrylate glycidyl ether, 3-hydroxypropyl (meth)acrylate glycidyl ether, 4-hydroxybutyl (meth)acrylate glycidyl ether), a $C_2$-$C_6$ isocyanatoalkyl (meth)acrylate, an aziridine-containing vinylic monomer (e.g., 3-(1-aziridinyl) propyl (meth)acrylate, 4-(1-aziridinyl) butyl (meth)acrylate, 6-(1-aziridinyl) hexyl (meth)acrylate, and 8-(1-aziridinyl) octyl (meth)acrylate), an azlactone-containing vinylic monomer (e.g., 2-vinyl-4,4-dimethyl-1,3-oxazolin-5-one, 2-isopropenyl-4,4-dimethyl-1,3-oxazolin-5-one, 2-vinyl-4-methyl-4-ethyl-1,3-oxazolin-5-one, 2-isopropenyl-4-methyl-4-butyl-1,3-oxazolin-5-one, 2-vinyl-4,4-dibutyl-1,3-oxazolin-5-one, 2-isopropenyl-4-methyl-4-dodecyl-1,3-oxazolin-5-one, 2-isopropenyl-4,4-diphenyl-1,3-oxazolin-5-one, 2-isopropenyl-4,4-pentamethylene-1,3-oxazolin-5-one, 2-isopropenyl-4,4-tetramethylene-1,3-oxazolin-5-one, 2-vinyl-4,4-diethyl-1,3-oxazolin-5-one, 2-vinyl-4-methyl-4-nonyl-1,3-oxazolin-5-one, 2-isopropenyl-4-methyl-4-phenyl-1,3-oxazolin-5-one, 2-isopropenyl-4-methyl-4-benzyl-1,3-oxazolin-5-one, 2-vinyl-4,4-pentamethylene-1,3-oxazolin-5-one, and 2-vinyl-4,4-dimethyl-1,3-oxazolin-6-one), a vinylic monomer having an aldehyde or $C_1$-$C_4$ alkylcarbonyl group (e.g., acrolein, methacrolein, crotonaldehyde, acrolein dimethyl acetal, acrolein diethyl acetal, methacrolein dimethyl acetal, methacrolein diethyl acetal, methyl vinyl ketone, 3-methyl-3-buten-2-one, 3-penten-2-one, ethyl vinyl ketone, propyl vinyl ketone, isopropyl vinyl ketone, vinyl butyl ketone, tert-butyl vinyl ketone, iso-butyl vinyl ketone, methyl allyl ketone).

An arylborono-containing vinyl-based copolymer of an arylborono-containing vinylic monomer and at least one hydrophilic vinylic monomer is a copolymerization product of a polymerizable composition which comprises (a) at least one arylborono-containing vinylic monomer and (b) at least one hydrophilic vinylic monomer. In accordance with this preferred embodiment, an arylborono-containing vinylic monomer is represented by formula (II)

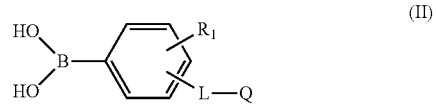

in which: $R_1$ is a monovalent radical (preferably is H, NO$_2$, F, Cl, Br, CF$_3$, CH$_2$OH, or CH$_2$NR$^o$R$^{o\prime}$ in which R$^o$ and R$^{o\prime}$ independent of each other are H or $C_1$-$C_4$ alkyl); Q is a monovalent radical of

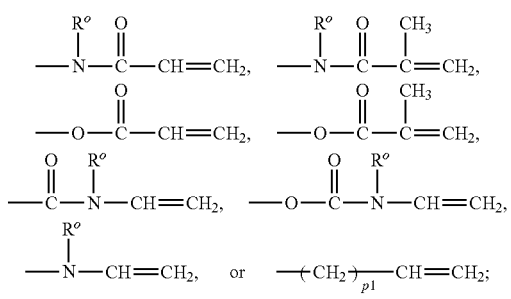

L is a direct bond, a $C_1$-$C_4$ alkylene divalent radical, a divalent radical of

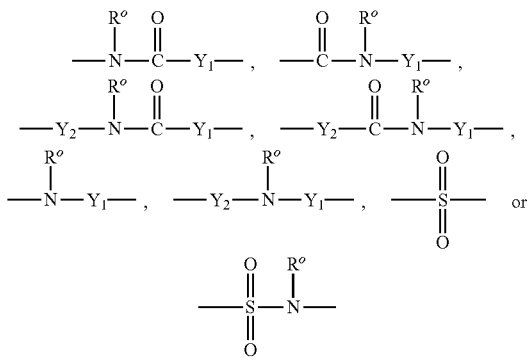

in which $Y_1$ is CH(OH) or a $C_1$-$C_4$ alkylene divalent radical, $Y_2$ is a $C_1$-$C_4$ alkylene divalent radical, p1 is an integer of 0 to 3, and $R^o$ is H or a $C_1$-$C_4$ alkyl.

Examples of preferred arylborono-containing vinylic monomers of formula (II) include without limitation 3-vinylphenylboronic acid, 4-vinylphenylboronic acid (pKa~8.8), 3-(meth)acrylamidophenylboronic acid (pKa~8.2), 4-(meth)acrylamidophenylboronic acid, 4-(1,6-Dioxo-2,5-diaza-7-oxamyl)phenylboronic acid (pKa~7.8), 2-Dimethylaminomethyl-5-vinylphenylboronic acid (pKa<7.8), 4-(N-allylsulfamoyl)phenylboronic acid (pKa~7.4), 4-(3-Butenylsulfonyl)phenylboronic acid (pKa~7.1), 3-(meth)acrylamido-5-nitrophenyl-boronic acid, 4-(meth)acrylamido-5-nitrophenylboronic acid, 4-(meth)acrylamido-3-nitrophenylboronic acid, 3-[(meth)acrylamido-$C_2$-$C_5$-alkylaminocarbonyl]-5-nitrophenyl-boronic acid, 3-[(meth)acryloyloxy-$C_2$-$C_5$-alkylaminocarbonyl]-5-nitrophenylboronic acid, 3-(meth)acrylamido-6-hydroxymethylphenylboronic acid, 3-(meth)acrylamido-6-dimethylaminomethylphenylboronic acid, 4-(meth)acrylamido-6-hydroxymethylphenyl-boronic acid, 4-(meth)acrylamido-6-dimethylaminomethylphenyl-boronic acid, a reaction production of an amino-containing phenylboronic acid derivative with (meth)acrylic acid halide, a reaction product of an amino-containing phenylboronic acid derivative with a carboxy-containing vinylic monomer in the presence of a carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl)carbodiimide, diisopropyl carbodiimide, or mixtures thereof) and N-hydroxysuccinimide, a reaction production of a carboxy-containing phenylboronic acid derivative with an amino-containing vinylic monomer in the presence of a carbodiimide (e.g., 1-ethyl-3-(3-dimethylaminopropyl) carbodiimide (EDC), N,N'-dicyclohexylcarbodiimide (DCC), 1-cylcohexyl-3-(2-morpholinoethyl)carbodiimide, diisopropyl carbodiimide, or mixtures thereof) and N-hydroxysuccinimide, and combinations thereof.

Examples of preferred carboxyl-containing phenylboronic acid derivatives include without limitation 3-carboxyphenylboronic acid, 4-carboxyphenylboronic acid, 3-boronophenylacetic acid, 4-boronophenylacetic acid, 2-(4-boronophenyl)-2-methyl-propanoic acid, 3-(4-boronophenyl)propanoic acid, 3-(3-boronophenyl) propanoic acid, 5-(3-boronophenyl)pentanoic acid, 5-(4-boronophenyl)pentanoic acid, 4-(2-carboxyethyl)-3-nitrophenylboronic acid, 3-carboxy-5-nitrophenylboronic acid, 4-carboxy-3-chlorophenyl-boronic acid, 3-carboxy-4-fluorophenylboronic acid, 3-(3-carboxypropyonylamino)phenyl-boronic acid, 3-amino-3-(4-boronophenyl)propanoic acid, and combinations thereof.

Examples of preferred amino-containing phenylboronic acid derivatives include without limitation 3-aminophenylboronic acid, 4-aminophenylboronic acid, 4-amino-3-nitrophenylboronic acid, 3-amino-6-hydroxymethylphenylboronic acid, 3-amino-6-(dimethylaminomethyl)phenylboronic acid, 4-amino-2-hydroxymethylphenylboronic acid, 4-amino-2-(dimethylaminomethyl)phenylboronic acid, 3-amino-4-fluorophenylboronic acid, 4-(aminomethyl)-5-nitrophenylboronic acid, 3-(aminomethyl)-phenylboronic acid, 3-amino-5-nitrophenylboronic acid, 3-amino-3-(4-boronophenyl)propanoic acid, and combinations thereof.

Examples of preferred acetal-containing phenylboronic acid derivatives include without limitation 2-acetoxyphenylboronic acid, 3-acetoxyphenylboronic acid, 4-acetoxyphenylboronic acid, 2-formylphenylboronic acid, 3-formylphenylboronic acid, 4-formylphenylboronic acid, 5-formyl-2-methoxyphenylboronic acid, 3-fluoro-4-formylphenylboronic acid, 4-fluoro-3-formylphenylboronic acid, and combinations thereof.

Examples of preferred bromide-containing phenylboronic acid derivatives include without limitation 2-(bromomethyl)-phenylboronic acid, 3-(bromomethyl)-phenylboronic acid, 4-(bromomethyl)-phenylboronic acid, and combinations thereof.

Examples of preferred hydroxy-containing phenylboronic acid derivatives include without limitation 3-chloro-4-hydroxyphenylboronic acid, 3-fluoro-5-hydroxyphenylboronic acid, 2-hydroxyphenylboronic acid, 3-hydroxyphenylboronic acid, 4-hydroxyphenylboronic acid, 2-(hydroxymethyl)phenylboronic acid, 3-(hydroxymethyl)phenylboronic acid, 4-(hydroxymethyl)phenylboronic acid, 3-(hydroxymethyl)-4-methoxyphenylboronic acid, and combinations thereof.

Examples of preferred thiol-containing phenylboronic acid derivatives include without limitation 3-mercaptophenylboronic acid, 4-mercaptophenylboronic acid, and combinations thereof.

Examples of preferred carboxy-containing vinylic monomer include without limitation 2-acrylamidoglycolic acid, 3-acrylamidopropionic acid, 4-acrylamidobutanoic acid, 5-acrylamidopentanoic acid, 3-acryloyloxypropanoic acid, 4-acryloyloxybutanoic acid, 5-acryloyloxypentanoic acid, and combinations thereof.

Examples of preferred amino-containing vinylic monomers include without limitation amino-$C_2$-$C_4$ alkyl (meth)acrylate, $C_1$-$C_3$ alkylamino-$C_2$-$C_4$ alkyl (meth)acrylate, amino-$C_2$-$C_4$ alkyl (meth)acrylamide, $C_1$-$C_3$ alkylamino-$C_2$-$C_4$ alkyl (meth)acrylamide, vinylamine, allylamine, and combinations thereof.

Any suitable hydrophilic vinylic monomers can be used in the preparation of the hydrophilic polymer and copolymer of an arylborono-containing vinylic monomer and at least one hydrophilic vinylic monomer. Examples of suitable hydrophilic vinylic monomers include without limitation carboxyl-containing vinylic monomers, primary amine-containing vinylic monomers, secondary amine-containing vinylic monomers, non-reactive hydrophilic vinylic monomers, phosphorylcholine-containing vinylic monomers, and combinations thereof.

Examples of preferred hydrophilic vinylic monomers are alkyl (meth)acrylamides (as described below), hydroxyl-containing acrylic monomers (as described below), amino-containing acrylic monomers (as described below), carboxyl-containing acrylic monomers (as described below), N-vinyl amide monomers (as described below), methylene-containing pyrrolidone monomers (i.e., pyrrolidone derivatives each having a methylene group connected to the pyrrolidone ring at 3- or 5-position) (as described below), acrylic monomers having a $C_1$-$C_4$ alkoxyethoxy group (as described below), vinyl ether monomers (as described below), allyl ether monomers (as described below), phosphorylcholine-containing vinylic monomers (as described below), N-2-hydroxyethyl vinyl carbamate, N-carboxyvinyl-β-alanine (VINAL), N-carboxyvinyl-α-alanine, and combinations thereof.

Examples of alkyl (meth)acrylamides includes without limitation (meth)acrylamide, N,N-dimethyl (meth)acrylamide, N-ethyl (meth)acrylamide, N,N-diethyl (meth)acrylamide, N-propyl (meth)acrylamide, N-isopropyl (meth)acrylamide, N-3-methoxypropyl (meth)acrylamide, and combinations thereof.

Examples of hydroxyl-containing acrylic monomers include without limitation N-2-hydroxyethyl (meth)acrylamide, N,N-bis(hydroxyethyl) (meth)acrylamide, N-3-hydroxypropyl (meth)acrylamide, N-2-hydroxypropyl (meth)acrylamide, 2-hydroxyethyl (meth)acrylate, 3-hydroxypropyl (meth)acrylate, 2-hydroxypropyl acrylate, di(ethylene glycol) (meth)acrylate, tri(ethylene glycol) (meth)acrylate, tetra(ethylene glycol) (meth)acrylate, poly(ethylene glycol) (meth)acrylate having a number average molecular weight of up to 1500, poly(ethylene glycol)ethyl (meth)acrylamide having a number average molecular weight of up to 1500, and combinations thereof.

Examples of amino-containing acrylic monomers include without limitation N-2-aminoethyl (meth)acrylamide, N-2-methylaminoethyl (meth)acrylamide, N-2-ethylaminoethyl (meth)acrylamide, N-2-dimethylaminoethyl (meth)acrylamide, N-3-aminopropyl (meth)acrylamide, N-3-methylaminopropyl (meth)acrylamide, N-3-dimethylaminopropyl (meth)acrylamide, 2-aminoethyl (meth)acrylate, 2-methylaminoethyl (meth)acrylate, 2-ethylaminoethyl (meth)acrylate, 3-aminopropyl (meth)acrylate, 3-methylaminopropyl (meth)acrylate, 3-ethylaminopropyl (meth)acrylate, 3-amino-2-hydroxypropyl (meth)acrylate, trimethylammonium 2-hydroxy propyl (meth)acrylate hydrochloride, dimethylaminoethyl (meth)acrylate, and combinations thereof.

Examples of carboxyl-containing acrylic monomers include without limitation 2-(meth)acrylamidoglycolic acid, (meth)acrylic acid, ethylacrylic acid, propylacrylic acid, 3-(meth)acrylamidopropionic acid, 4-(meth)acrylamidobutanoic acid, 5-(meth)acrylamidopentanoic acid, 3-(meth)acryloyloxypropanoic acid, 4-(meth)acryloyloxybutanoic acid, 5-(meth)acryloyloxypentanoic acid, and combinations thereof.

Examples of preferred N-vinyl amide monomers include without limitation N-vinylpyrrolidone (aka, N-vinyl-2-pyrrolidone), N-vinyl-3-methyl-2-pyrrolidone, N-vinyl-4-methyl-2-pyrrolidone, N-vinyl-5-methyl-2-pyrrolidone, N-vinyl-6-methyl-2-pyrrolidone, N-vinyl-3-ethyl-2-pyrrolidone, N-vinyl-4,5-dimethyl-2-pyrrolidone, N-vinyl-5,5-dimethyl-2-pyrrolidone, N-vinyl-3,3,5-trimethyl-2-pyrrolidone, N-vinyl piperidone (aka, N-vinyl-2-piperidone), N-vinyl-3-methyl-2-piperidone, N-vinyl-4-methyl-2-piperidone, N-vinyl-5-methyl-2-piperidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl caprolactam (aka, N-vinyl-2-caprolactam), N-vinyl-3-methyl-2-caprolactam, N-vinyl-4-methyl-2-caprolactam, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, N-vinyl-N-methyl acetamide, N-vinyl formamide, N-vinyl acetamide, N-vinyl isopropylamide, N-vinyl-N-ethyl acetamide, N-vinyl-N-ethyl formamide, and mixtures thereof. Preferably, the N-vinyl amide monomer is N-vinylpyrrolidone, N-vinyl-N-methyl acetamide, or combinations thereof.

Examples of preferred methylene-containing (=$CH_2$) pyrrolidone monomers include without limitations 1-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, and combinations thereof.

Examples of preferred acrylic monomers having a $C_1$-$C_4$ alkoxyethoxy group include without limitation ethylene glycol methyl ether (meth)acrylate, di(ethylene glycol) methyl ether (meth)acrylate, tri(ethylene glycol) methyl ether (meth)acrylate, tetra(ethylene glycol) methyl ether (meth)acrylate, $C_1$-$C_4$-alkoxy poly(ethylene glycol) (meth)acrylate having a weight average molecular weight of up to 1500, methoxy-poly(ethylene glycol)ethyl (meth)acrylamide having a number average molecular weight of up to 1500, and combinations thereof.

Examples of preferred vinyl ether monomers include without limitation ethylene glycol monovinyl ether, di(ethylene glycol) monovinyl ether, tri(ethylene glycol) monovinyl ether, tetra(ethylene glycol) monovinyl ether, poly(ethylene glycol) monovinyl ether, ethylene glycol methyl vinyl ether, di(ethylene glycol) methyl vinyl ether, tri(ethylene glycol) methyl vinyl ether, tetra(ethylene glycol) methyl vinyl ether, poly(ethylene glycol) methyl vinyl ether, and combinations thereof.

Examples of preferred allyl ether monomers include without limitation allyl alcohol, ethylene glycol monoallyl ether, di(ethylene glycol) monoallyl ether, tri(ethylene glycol) monoallyl ether, tetra(ethylene glycol) monoallyl ether, poly(ethylene glycol) monoallyl ether, ethylene glycol methyl allyl ether, di(ethylene glycol) methyl allyl ether, tri(ethylene glycol) methyl allyl ether, tetra(ethylene glycol) methyl allyl ether, poly(ethylene glycol) methyl allyl ether, and combinations thereof.

Examples of preferred phosphorylcholine-containing vinylic monomers include without limitation (meth)acryloyloxyethyl phosphorylcholine (aka, MPC, or 2-((meth)acryloyloxy)ethyl-2'-(trimethylammonio)ethylphosphate), (meth)acryloyloxypropyl phosphorylcholine (aka, 3-((meth)acryloyloxy)propyl-2'-(trimethylammonio)ethylphosphate), 4-((meth)acryloyloxy)butyl-2'-(trimethylammonio)ethylphosphate, 2-[(meth)acryloylamino]-ethyl-2'-(trimethylammonio)-ethylphosphate, 3-[(meth)acryloylamino]propyl-2'-(trimethyl-ammonio)ethylphosphate, 4-[(meth)acryloylamino]butyl-2'-(trimethylammonio)ethyl-phosphate, 5-((meth)acryloyloxy)pentyl-2'-(trimethylammonio)ethyl phosphate, 6-((meth)acryloyloxy)hexyl-7-(trimethylammonio)-ethylphosphate, 2-((meth)acryloyloxy)ethyl-2'-(triethylammonio)ethylphosphate, 2-((meth)acryloyloxy)ethyl-2'-(tripropylammonio)ethyl-phosphate, 2-((meth)acryloyloxy)ethyl-2'-(tributylammonio)ethyl phosphate, 2-((meth)acryloyloxy)propyl-2'-(trimethylammonio)-ethylphosphate, 2-((meth)acryloyloxy)-butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethyl phosphate, 2-(vinyloxy)ethyl-2'-(trimethylammonio)ethylphosphate, 2-(allyloxy)ethyl-2'-(trimethylammonio)ethylphosphate, 2-(vinyloxycarbonyl) ethyl-2'-(trimethylammonio)ethyl phosphate, 2-(allyloxycarbonyl)ethyl-2'-(trimethylammonio)-ethylphosphate, 2-(vinylcarbonylamino)ethyl-2'-(trimethylammonio)ethylphosphate, 2-(allyloxycarbonylamino)-ethyl-7-(trimethylammonio)ethyl phosphate, 2-(butenoyloxy)ethyl-2'-(trimethylammonio)-ethylphosphate, and combinations thereof.

Examples of preferred acrylic monomers having 3 to 16 carbon atoms include without limitation $C_1$-$C_{12}$ alkyl (meth)acrylates, hydroxy-substituted $C_2$-$C_{12}$ alkyl (meth)acrylates, carboxy-substituted $C_2$-$C_{12}$ alkyl (meth)acrylates, $NH_2$-substituted $C_2$-$C_{12}$ alkyl (meth)acrylates, methylamino-substituted $C_2$-$C_{12}$ alkyl (meth)acrylates, dimethylamino-substituted $C_2$-$C_{12}$ alkyl (meth)acrylates, ethylamino-substituted $C_2$-$C_{10}$ alkyl (meth)acrylates, diethylamino-substituted $C_2$-$C_8$ alkyl (meth)acrylates, $C_2$-$C_{12}$ alkyl (meth)acrylamides, hydroxy-substituted $C_2$-$C_{12}$ alkyl (meth)acrylamides, carboxy-substituted $C_2$-$C_{12}$ alkyl (meth)acrylaides, $NH_2$-substituted $C_2$-$C_{12}$ alkyl (meth)acrylamides, methylamino-substituted $C_2$-$C_{12}$ alkyl (meth)acrylamides, dimethylamino-substituted $C_2$-$C_{12}$ alkyl (meth)acrylamides, ethylamino-substituted $C_2$-$C_{10}$ alkyl (meth)acrylamides, diethylamino-substituted $C_2$-$C_8$ alkyl (meth)acrylamides, ethylene glycol (meth)acrylate, di(ethylene glycol) (meth)acrylate, tri(ethylene glycol) (meth)acrylate, tetra(ethylene glycol) (meth)acrylate, ethylene glycol methyl ether (meth)acrylate, di(ethylene glycol) methyl ether (meth)acrylate, tri(ethylene glycol) methyl ether (meth)acrylate, tetra(ethylene glycol) methyl ether (meth)acrylate, and combinations thereof.

In a preferred embodiment, the arylborono-containing hydrophilic copolymer comprises (a) from about 0.1% by mole to about 25% by mole (preferably from about 1% to about 20% by mole, more preferably from about 2% to about 20% by mole, even more preferably from about 3% to about 18% by mole) of arylborono-containing repeating units each having an arylborono group and (b) from about 75% by mole to about 99.9% by mole (preferably from about 80% to about 99% by mole, more preferably from about 80% to about 98% by mole, even more preferably from about 82% to about 97% by mole) of repeating units of at least one hydrophilic vinylic monomer, provided that the sum of the mole percentages of components (a) and (b) and other components not listed above is 100%. In a preferred embodiment, the arylborono group has a pKa of from about 6.8 to 9.2, preferably from about 7.0 to about 9.0, more preferably from about 7.2 to about 8.8, even more preferably from about 7.4 to about 8.6.

In another preferred embodiment, the hydrophilic copolymer comprises (a) from about 0.1% to about 25% by mole (preferably from about 1% to about 20% by mole, more preferably from about 2% to about 18% by mole) of arylborono-containing repeating units each having an arylborono group, (b) from about 55% to about 98.9% by mole (preferably from about 60% to about 97% by mole, more preferably from about 70% to about 95% by mole) of repeating units of at least one phosphorylcholine-containing vinylic monomer, and (c) from about 1% by mole to about 20% by mole (preferably from about 2% to about 15% by mole, more preferably from about 3% to about 20% by mole) of acrylic monomeric units of at least one acrylic monomer having 3 to 16 (preferably 3 to 14, more preferably 3 to 12, even more preferably 3 to 10) carbon atoms, provided that the sum of the mole percentages of components (a), (b) and (c) and other components not listed above is 100%. In a preferred embodiment, the arylborono group has a pKa of from about 6.8 to 9.2, preferably from about 7.0 to about 9.0, more preferably from about 7.2 to about 8.8, even more preferably from about 7.4 to about 8.6.

In accordance with the invention, the mole percentages of each type of repeating units (i.e., monomeric units) of an arylborono-containing hydrophilic copolymer can be determined based on the mole percentage of a vinylic monomer, from which this type of repeating units are derived, in a polymerizable composition for forming the preformed hydrophilic polymer or the arylborono-containing vinyl-based copolymer.

In accordance with the invention, an arylborono-containing hydrophilic copolymer of the invention has a number average molecular weight of from about 5,000 Daltons to 500,000 Daltons, preferably from about 5,000 Daltons to about 400,000 Daltons, more preferably from about 5,000 Daltons to about 250,000 Daltons.

In accordance with the invention, any linear or branched mucoadhesive polymer can be used in the invention, so long as it has reactive moieties selected from the group consisting of 1,2-diol moieties, 1,3-diol moieties, α-hydroxycarboxylic acid moieties, β-hydroxycarboxylic acid moieties, and combinations thereof.

Examples of preferred mucoadhesive polymers include without limitation dextran, mannan, hyaluronic acid, a galactomannan polymer, polyvinyl alcohol, and combinations thereof.

As used in this application, a galactomannan polymer refers to a galactomannan (e.g., guar) and/or a chemically modified galactomannan.

A galactomannan, as known to a person skilled in the art, is a polysaccharide consisting of a mannose backbone with galactose side groups (more specifically, a (1-4)-linked beta-D-mannopyranose backbone with branch points from their 6-positions linked to alpha-D-galactose, (i.e. 1-6-linked alpha-D-galactopyranose). The ratio of D-galactose to D-mannose in galactomannan can vary, but generally will be from about 1:2 to 1:4. Galactomannans having a D-galactose:D-mannose ratio of about 1:2 are most preferred. Preferred galactomannan is guar.

Galactomannans may be obtained from numerous sources. Such sources include guar gum, locust bean gum and tara gum, as further described below.

Guar gum is the ground endosperm of *Cyamopisis tetragonolobus* (L.) Taub. The water soluble fraction (85%) is called "guaran" (molecular weight of 220,000), which consists of linear chains of (1-4)-β-D mannopyranosyl units with α-D-galactopyranosyl units attached by (1-6) linkages. The ratio of D-galactose to D-mannose in guaran is about 1:2. The gum has been cultivated in Asia for centuries and is primarily used in food and personal care products for its thickening property. It has five to eight times the thickening power of starch. Guar gum may be obtained, for example, from Rhone-Polulenc (Cranbury, N.J.), Hercules, Inc. (Wilmington, Del.) and TIC Gum, Inc. (Belcamp, Md.).

Locust bean gum or carob bean gum is the refined endosperm of the seed of the carob tree, *Ceratonia siliqua*. The ratio of galactose to mannose for this type of gum is about 1:4. Cultivation of the carob tree is old and well known in the art. This type of gum is commercially available and may be obtained from TIC Gum, Inc. (Bekamp, Md.) and Rhone-Polulenc (Cranbury, N.J.).

Tara gum is derived from the refined seed gum of the tara tree. The ratio of galactose to mannose is about 1:3. Tara gum is not produced in the United States commercially, but the gum may be obtained from various sources outside the United States.

A chemically-modified galactomannan is a derivative of a galactomannan in which some (but not all) of hydrogen atoms of the hydroxyl groups are substituted with an organic group. Examples of preferred chemically-modified glactomannans includes without limitation hydroxyethyl-substituted galactomannan (e.g., hydroxyethyl guar), hydroxypropyl galactomannan (e.g., hydroxypropyl guar), $C_1$-$C_3$ alkyl galactomannan (e.g., methyl guar, ethyl guar, propyl guar), carboxymethyl galactomannan (e.g., carboxymethyl guar), carboxymethylhydroxypropyl galactomannan (e.g., carboxymethylhydroxypropyl guar), hydroxypropyltrimonium chloride galactomannan (e.g., hydroxypropyltrimonium chloride guar), and combinations thereof. Preferred chemically-modified glactomannans are hydroxypropyl guar.

Hydroxyethyl guar, hydroxypropyl guar, methyl guar, ethyl guar, propyl guar, carboxymethyl guar, carboxymethylhydroxypropyl guar, and hydroxypropyltrimonium chloride guar are well known and are commercially available. For example, modified galactomannans of various degree of substitution are commercially available from Rhone-Poulenc (Cranbury, N.J.).

In some embodiments, the one or more mucoadhesive polymers are present in an amount of from about 50% to about 99% w/w, about 60% to about 99% w/w, about 70% to about 98% w/w, or about 80% to about 98% w/w by dry weight of the ocular insert. In particular embodiments, the mucoadhesive polymers are present in an amount of about 75%, about 80%, about 85%, about 90%, or about 95% w/w by dry weight of the ocular insert. The overall dry weight or mass of the ocular insert may be in the range of about 1 to about 10 mg, or about 2 to about 8 mg, and in particular embodiments may be from about 2.5 to about 5 mg.

In some embodiments, the ocular insert may have a water content of from about 10% to about 70% (preferably from about 20% to about 65%, more preferably from about 25% to about 60%, even more preferably from about 30% to about 55%) by weight (w/w) after being fully hydrated.

The ocular insert may be of any size or shape suitable for administration to the eye. Exemplary shapes include film, a rod, a sphere, an oval, a ring, a square, a rectangle, a triangle, or an irregular shape having a maximum size in any single dimension of 5-6 mm.

In some embodiments, the ocular insert has a thickness of about 50-400 μm, about 60-300 μm, or about 60-250 μm.

In particular embodiments, the ocular insert has a thickness of about 60-250 μm, and a water content of 20 to 55% w/w.

In some embodiments, the ocular insert of the invention can have an on-eye dissolution time of at least 3 hours, preferably at least 4 hours, more preferably from about 4 to 24 hours. The on-eye dissolution time can be determined by determining the dissolution time of an ocular insert in an artificial tear fluid (ATF) know to a person skilled in the art. The dissolution time of an ocular insert of the invention can be fine-tuned by selecting a desired pKa (i.e., the hydrolysis stability of the cyclic boronic ester crosslinks) of the arylborono groups of an arylborono-containing hydrophilic copolymer used in forming the ocular insert and the contents (i.e., the density of the cyclic boronic ester crosslinks) of the arylborono-containing repeating units of the arylborono-containing hydrophilic copolymer.

In some embodiments, an ocular insert has a multilayered structure and comprises a first hydrogel layer sandwiched between two second hydrogel layers, wherein the first hydrogel layer has a first crosslinking density of first crosslinks and the second hydrogel layers have a second crosslinking density of second crosslinks, wherein the first crosslinking density is higher than the second crosslinking density and/or the first crosslinks are more stable than the second crosslinks (i.e., hydrolyzing more slowly than the second crosslinks in the tear of the eye). With such a layered structure, an ocular insert of the invention can have a well-controlled disintegration kinetics for each layers, i.e., the outer hydrogel layers can be disintegrated (dissolved) first whereas the inner layer can be disintegrated (dissolved) later. Such an ocular insert can offer more flexibility to tune properties of selected layers to achieve desired overall dissolution profile.

In some embodiments of the present disclosure, the ocular insert does not include an additional pharmaceutically active agent. The mucoadhesive polymer making up the ocular insert may slowly be released in the eye due to the slowly disintegration of the hydrogel body of the ocular insert, thereby relieving the symptoms associated with dry eye.

In other embodiments, the polymeric eye insert may include one or more additional pharmaceutically active agents. In some embodiments, the one or more pharmaceutically active agents may be selected from the group of ocular lubricants, anti-redness relievers such as brimonidine tartrate, tetrahydrozoline, naphazoline, cooling agents such as menthol, steroids and nonsteroidal anti-inflammatory agents to relieve ocular pain and inflammation, antibiotics, anti-histamines such as olopatadine, anti-virals, antibiotics and anti-bacterials for infectious conjunctivitis, anti-muscarinics such as atropine and derivatives thereof for myopia treatment, and glaucoma drug delivery such as prostaglandin and prostaglandin analogs such as travoprost, or therapeutically suitable combinations thereof.

In some embodiments, an ocular insert of the invention is stored in a packaging aqueous solution in a sealed and sterilized package.

The packaging aqueous solution has a pH of from about 7.5 to about 9.0. The packaging aqueous solution contains a buffering agent in an amount sufficient to maintain a pH of the packaging aqueous solution in the desired range. Any known, physiologically compatible buffering agents can be used. Preferably, the buffering agents are phosphate buffers. The amount of each buffer agent in a packaging aqueous solution is preferably from 0.001% to 2%, preferably from 0.01% to 1%; most preferably from about 0.05% to about 0.30% by weight.

The packaging aqueous solution has a tonicity of from about 200 to about 450 milliosmol (mOsm), preferably from about 250 to about 350 mOsm. The tonicity of a packaging aqueous solution can be adjusted by adding organic or inorganic substances which affect the tonicity. Suitable occularly acceptable tonicity agents include, but are not limited to sodium chloride, potassium chloride, and mixtures thereof.

Packages (or containers) are well known to a person skilled in the art for autoclaving and storing ocular inserts. Any packages can be used in the invention.

In a preferred embodiment, the packaging aqueous solution contains at least one buffering agent and one or more other ingredients known to a person skilled in the art. Examples of other ingredients include without limitation, tonicity agents, surfactants, antibacterial agents, preservatives, and lubricants (e.g., cellulose derivatives, polyvinyl alcohol, polyvinylpyrrolidone).

Ocular inserts according to embodiments of the present disclosure may be made by curing a reactive composition to form a hydrogel, wherein the water-based reactive composition comprises at least one arylborono-containing hydrophilic copolymer (as described above) and at least one mucoadhesive polymer (as described above) both dissolved in a solvent (water, an organic solvent, or a mixture thereof).

The curing can be carried out by mixing one first solution of at least one arylborono-containing hydrophilic copolymer with one second solution of at least one mucoadhesive hydrophilic polymer in a mold to obtain a reactive composition having a pH at which said at least one arylborono-containing hydrophilic copolymer and said at least one mucoadhesive polymer are crosslinked through crosslinks each formed between one arylborono group of the arylborono-containing hydrophilic copolymer and one 1,2-diol, 1,3-diol, α-hydroxycarboxylic acid, or β-hydroxycarboxylic acid moiety of the mucoadhesive polymer.

Alternatively, the curing can be carried out by increasing the pH of a solution containing a mixture of at least one arylborono-containing hydrophilic copolymer and at least one mucoadhesive hydrophilic polymer in a mold to a pH at which said at least one arylborono-containing hydrophilic copolymer and said at least one mucoadhesive polymer are crosslinked through crosslinks each formed between one arylborono group of the arylborono-containing hydrophilic copolymer and one 1,2-diol, 1,3-diol, α-hydroxycarboxylic acid, or β-hydroxycarboxylic acid moiety of the mucoadhesive polymer. Preferably, the increasing of pH is carried out by adding a base solution having a pH of about 10.0 or higher.

Any molds known to a person skilled in the art can be used in the invention. Examples of preferred molds include without limitation a flat mold for film or thin sheet casting or for rod casting, reactive injection molds having the final 3-dimensional shapes of ocular inserts. The cast molded films, sheets, or rods can be machined to form the final 3-dimensional shapes of ocular inserts.

In accordance with the invention, the formed hydrogel ocular insert can be extracted to remove unreactive components and hydrated to with water or an aqueous solution to replace any organic solvent and equilibrate with water. Preferably, the aqueous solution has a pH for stabilizing the hydrogel and fully hydrating the hydrogel. The formed ocular inserts can also be sterilized according to any techniques known to a person skilled in the art.

In another aspect, the invention provides a method for producing hydrogel ocular inserts for treating a disease or disorder of an eye of a subject, comprising the steps of: (1) curing a reactive composition to form a hydrogel which is in a form of an ocular insert or is machined into the form of the ocular insert, wherein the reactive composition comprises said at least one arylborono-containing hydrophilic copolymer and said at least one mucoadhesive polymer both dissolved in a solvent, wherein said at least one arylborono-containing hydrophilic copolymer comprises repeating units each having an arylborono group, wherein said at least one mucoadhesive polymer comprises repeating units each having a moiety selected from the group consisting of 1,2-diol moiety, 1,3-diol moiety, α-hydroxycarboxylic acid moiety, and p-hydroxycarboxylic acid moiety, wherein the hydrogel is a crosslinking product of said at least one arylborono-containing hydrophilic copolymer and said at least one mucoadhesive polymer and comprises crosslinks each formed between one arylborono group of the arylborono-containing hydrophilic copolymer and one 1,2-diol, 1,3-diol, α-hydroxycarboxylic acid, or p-hydroxycarboxylic acid moiety of the mucoadhesive polymer; (2) contacting the hydrogel with an aqueous solution having a pH for stabilizing the hydrogel and fully hydrating the hydrogel; and (3) sterilizing the hydrogel.

In some embodiments, a method of the invention further comprises step of sealing the hydrogel ocular insert immersed in the aqueous solution in a package and autoclaving the sealed package at a temperature of from about 115° C. to about 125° C. for approximately 20-90 minutes.

In a further aspect, the invention provides a method for using of a hydrogel ocular insert of the invention (as described above) for treating a disease or disorder of an eye of a subject, comprising administering the hydrogel ocular insert into the eye.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A hydrogel ocular insert, comprising a hydrogel material, wherein the hydrogel material is a crosslinked polymeric material which is a crosslinking product of at least one arylborono-containing hydrophilic copolymer including arylborono-containing repeating units each having an arylborono group and at least one mucoadhesive polymer including repeating units each having a moiety selected from the group consisting of 1,2-diol moiety, 1,3-diol moiety, α-hydroxycarboxylic acid moiety, and β-hydroxycarboxylic acid moiety, wherein said at least one arylborono-containing hydrophilic copolymer and said at least one mucoadhesive polymer are crosslinked in the crosslinked polymeric material through crosslinks each formed between one of arylborono groups of said at least one arylborono-containing hydrophilic copolymer and one 1,2-diol, 1,3-diol, α-hydroxycarboxylic acid, or 8-hydroxycarboxylic acid moiety of said at least one mucoadhesive polymer.

2. The hydrogel ocular insert of embodiment 1, wherein said at least one arylborono-containing hydrophilic copolymer comprises an arylborono-modified hydrophilic polymer.

3. The hydrogel ocular insert of embodiment 2, wherein the arylborono-modified hydrophilic polymer is a coupling reaction product of a phenylboronic acid compound and a preformed hydrophilic polymer, wherein the phenylboronic acid compound has a first reactive functional group, wherein the preformed hydrophilic polymer comprises repeating monomeriuc units each having a second reactive function group which is coreactive with the first reactive functional group in the presence or absence of a coupling agent to form a covalent linkage, wherein the first and second reactive functional groups independent of each other are selected from the group consisting of hydroxyl group (—OH), carboxyl group (—COOH), acid halide group, —NH$_2$, C$_1$-C$_4$ alkylamino group, epoxy group, aldehyde group, isocyanato group, azlactone group, azidirine group, and thiol group.

4. The hydrogel ocular insert of embodiment 3, wherein the preformed hydrophilic polymer is a homopolymer or copolymer of a vinylic monomer selected from the group consisting of $C_2$-$C_4$-hydroxyalkyl (meth)acrylate, $C_2$-$C_4$-hydroxyalkyl (meth)acrylamide, allylalcohol, allylamine, vinylamine, amino-$C_2$-$C_4$-hydroxyalkyl (meth)acrylate, amino-$C_2$-$C_4$-hydroxyalkyl (meth)acrylamide, $C_1$-$C_3$ alkylamino-$C_2$-$C_4$ alkyl (meth)acrylate, $C_1$-$C_3$ alkylamino-$C_2$-$C_4$ alkyl (meth)acrylamide, glycerol (meth)acrylate, N-(2,3-dihydroxypropyl) (meth)acrylamide, N,N-bis(2-hydroxyethyl) (meth)acrylamide, N-tris(hydroxymethyl)methyl (meth)acrylamide, (meth)acrylic acid halide (chloride, bromide, or iodide), (meth)acrylic anhydride, maleic anhydride, acrylic acid, and $C_1$-$C_4$ alkylacrylic acid (e.g., methacrylic ethylacrylic acid, propylacrylic acid, butylacrylic acid), 2-acrylamidoglycolic acid, 3-acrylamidopropionic acid, 4-acrylamidobutanoic acid, 5-acrylamidopentanoic acid, 3-acryloyloxypropanoic acid, 4-acryloyloxybutanoic acid, 5-acryloyloxypentanoic acid, an epoxy-containing vinylic monomer (e.g., glycidyl (meth)acrylamide, hydroxyethyl (meth)acrylamide glycidyl ether, 3-hydroxypropyl (meth)acrylamide glycidyl ether, 4-hydroxybutyl (meth)acrylamide glycidyl ether, glycidyl (meth)acrylate, hydroxyethyl (meth)acrylate glycidyl ether, 3-hydroxypropyl (meth)acrylate glycidyl ether, 4-hydroxybutyl (meth)acrylate glycidyl ether), a $C_2$-$C_6$ isocyanatoalkyl (meth)acrylate, an aziridine-containing vinylic monomer (e.g., 3-(1-aziridinyl) propyl (meth)acrylate, 4-(1-aziridinyl) butyl (meth)acrylate, 6-(1-aziridinyl) hexyl (meth)acrylate, and 8-(1-aziridinyl) octyl (meth)acrylate), an azlactone-containing vinylic monomer (e.g., 2-vinyl-4,4-dimethyl-1,3-oxazolin-5-one, 2-isopropenyl-4,4-dimethyl-1,3-oxazolin-5-one, 2-vinyl-4-methyl-4-ethyl-1,3-oxazolin-5-one, 2-isopropenyl-4-methyl-4-butyl-1,3-oxazolin-5-one, 2-vinyl-4,4-dibutyl-1,3-oxazolin-5-one, 2-isopropenyl-4-methyl-4-dodecyl-1,3-oxazolin-5-one, 2-isopropenyl-4,4-diphenyl-1,3-oxazolin-5-one, 2-isopropenyl-4,4-pentamethylene-1,3-oxazolin-5-one, 2-isopropenyl-4,4-tetramethylene-1,3-oxazolin-5-one, 2-vinyl-4,4-diethyl-1,3-oxazolin-5-one, 2-vinyl-4-methyl-4-nonyl-1,3-oxazolin-5-one, 2-isopropenyl-4-methyl-4-phenyl-1,3-oxazolin-5-one, 2-isopropenyl-4-methyl-4-benzyl-1,3-oxazolin-5-one, 2-vinyl-4,4-pentamethylene-1,3-oxazolin-5-one, and 2-vinyl-4,4-dimethyl-1,3-oxazolin-6-one), a vinylic monomer having an aldehyde or $C_1$-$C_4$ alkylcarbonyl group (e.g., acrolein, methacrolein, crotonaldehyde, acrolein dimethyl acetal, acrolein diethyl acetal, methacrolein dimethyl acetal, methacrolein diethyl acetal, methyl vinyl ketone, 3-methyl-3-buten-2-one, 3-penten-2-one, ethyl vinyl ketone, propyl vinyl ketone, isopropyl vinyl ketone, vinyl butyl ketone, tert-butyl vinyl ketone, iso-butyl vinyl ketone, methyl allyl ketone).

5. The hydrogel ocular insert of any one of embodiments 1 to 4, wherein said at least one arylborono-containing hydrophilic copolymer comprises an arylborono-containing vinyl-based copolymer comprising (a) arylborono-containing repeating units of at least one arylborono-containing vinylic monomer and (b) hydrophilic repeating units of at least one hydrophilic vinylic monomer.

6. The hydrogel ocular insert of embodiment 5, wherein said at least one arylborono-containing vinylic monomer is represented by formula (II)

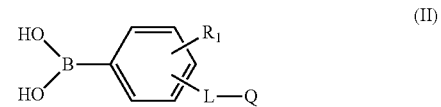

in which: $R_1$ is a monovalent radical; Q is a monovalent radical of

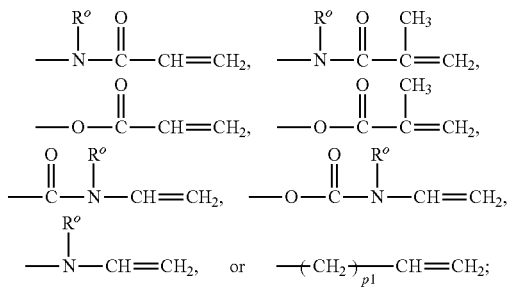

L is a direct bond, a $C_1$-$C_4$ alkylene divalent radical, a divalent radical of

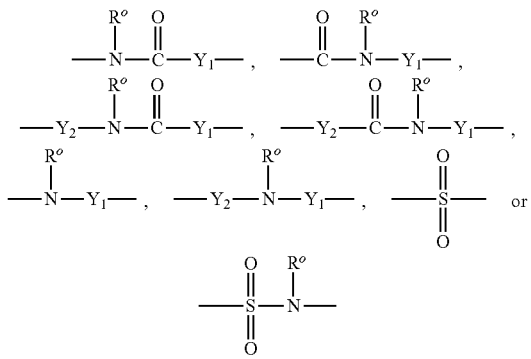

in which $Y_1$ is CH(OH) or a $C_1$-$C_4$ alkylene divalent radical, $Y_2$ is a $C_1$-$C_4$ alkylene divalent radical, p1 is an integer of 0 to 3, and $R^o$ is H or a $C_1$-$C_4$ alkyl.

7. The hydrogel ocular insert of embodiment 6, wherein in formula (II) $R_1$ is H, $NO_2$, F, Cl, Br, $CF_3$, $CH_2OH$, or $CH_2NR^oR^{o\prime}$ in which $R^o$ and $R^{o\prime}$ independent of each other are H or $C_1$-$C_4$ alkyl.

8. The hydrogel ocular insert of any one of embodiments 5 to 7, wherein said at least one arylborono-containing vinylic monomer is selected from the group consisting of 3-vinylphenylboronic acid, 4-vinylphenylboronic acid, 3-(meth)acrylamidophenylboronic acid, 4-(meth)acrylamidophenylboronic acid, 3-(meth)acrylamido-5-nitrophenylboronic acid, 4-(meth)acrylamido-5-nitrophenylboronic acid, 4-(meth)acrylamido-3-nitrophenylboronic acid, 3-[(meth)acrylamido-$C_2$-$C_5$-alkylaminocarbonyl]-5-nitrophenylboronic acid, 3-[(meth)acryloyloxy-$C_2$-$C_5$-alkylaminocarbonyl]-5-nitrophenylboronic acid, 3-(meth)acrylamido-6-hydroxymethylphenylboronic acid, 3-(meth)acrylamido-6-dimethylaminomethylphenylboronic acid, 4-(meth)acrylamido-6-hydroxymethylphenylboronic acid, 4-(meth)acrylamido-6-dimethylaminomethylphenylboronic acid, 4-(1,6-Dioxo-2,5-diaza-7-oxamyl)phenylboronic acid, 4-(N-allylsulfamoyl)phenylboronic acid, 4-(3-butenylsulfonyl)phenylboronic acid, and combinations thereof.

9. The hydrogel ocular insert of any one of embodiments 5 to 7, wherein said at least one arylborono-containing vinylic monomer is selected from the group consisting of a reaction production of an amino-containing phenylboronic acid derivative with (meth)acrylic acid halide, a reaction product of an amino-containing phenylboronic acid derivative with a carboxy-containing vinylic monomer in the presence of a carbodiimide and N-hydroxysuccinimide, a reaction production of a carboxy-containing phenylboronic acid derivative with an amino-containing vinylic monomer in the presence of a carbodiimide and N-hydroxysuccinimide, and combinations thereof.

10. The hydrogel ocular insert of embodiment 9, wherein the carboxy-containing phenylboronic acid derivative is selected from the group consisting of 3-carboxyphenylboronic acid, 4-carboxyphenylboronic acid, 3-boronophenylacetic acid, 4-boronophenylacetic acid, 2-(4-boronophenyl)-2-methylpropanoic acid, 3-(4-boronophenyl)propanoic acid, 3-(3-boronophenyl)propanoic acid, 5-(3-boronophenyl)pentanoic acid, 5-(4-boronophenyl)pentanoic acid, 4-(2-carboxyethyl)-3-nitrophenylboronic acid, 3-carboxy-5-nitrophenylboronic acid, 4-carboxy-3-chlorophenylboronic acid, 3-carboxy-4-fluorophenylbornic acid, 3-(3-carboxypropyonylamino)phenylboronic acid, 3-amino-3-(4-boronophenyl)propanoic acid, and combinations thereof,
   wherein the amino-containing phenylboronic acid derivative is selected from the group consisting of 3-aminophenylboronic acid, 4-aminophenylboronic acid, 4-amino-3-nitrophenylboronic acid, 3-amino-6-hydroxymethylphenylboronic acid, 3-amino-6-(dimethylaminomethyl)phenylboronic acid, 4-amino-2-hydroxymethylphenylboronic acid, 4-amino-2-(dimethylaminomethyl)phenylboronic acid, 3-amino-4-fluorophenylboronic acid, 4-(aminomethyl)-5-nitrophenylboronic acid, 3-(aminomethyl)-phenylboronic acid, 3-amino-5-nitrophenylboronic acid, 3-amino-3-(4-boronophenyl)propanoic acid, and combinations thereof,
   wherein the carboxyl-containing vinylic monomer is selected from the group consisting of 2-acrylamidoglycolic acid, 3-acrylamidopropionic acid, 4-acrylamidobutanoic acid, 5-acrylamidopentanoic acid, 3-acryloyloxypropanoic acid, 4-acryloyloxybutanoic acid, 5-acryloyloxypentanoic acid, and combinations thereof,
   wherein the amino-containing vinylic monomers is selected from the group consisting of amino-$C_2$-$C_4$ alkyl (meth)acrylate, $C_1$-$C_3$ alkylamino-$C_2$-$C_4$ alkyl (meth)acrylate, amino-$C_2$-$C_4$ alkyl (meth)acrylamide, $C_1$-$C_3$ alkylamino-$C_2$-$C_4$ alkyl (meth)acrylamide, vinylamine, allylamine, and combinations thereof.

11. The hydrogel ocular insert of any one of embodiments 5 to 10, wherein said at least one hydrophilic vinylic monomer comprises a phosphorylcholine-containing vinylic monomer.

12. The hydrogel ocular insert of any one of embodiments 5 to 11, wherein said at least one hydrophilic vinylic monomer comprises a vinylic monomer selected from the group consisting of (meth)acrylamide, N,N-dimethyl (meth)acrylamide, N-ethyl (meth)acrylamide, N,N-diethyl (meth)acrylamide, N-propyl (meth)acrylamide, N-isopropyl (meth)acrylamide, N-3-methoxypropyl (meth)acrylamide, and combinations thereof.

13. The hydrogel ocular insert of any one of embodiments 5 to 12, wherein said at least one hydrophilic vinylic monomer comprises a vinylic monomer selected from the group consisting of N-2-hydroxyethyl (meth)acrylamide, N,N-bis(hydroxyethyl) (meth)acrylamide, N-3-hydroxypropyl (meth)acrylamide, N-2-hydroxypropyl (meth)acrylamide, 2-hydroxyethyl (meth)acrylate, 3-hydroxypropyl (meth)acrylate, 2-hydroxypropyl (meth)acrylate, di(ethylene glycol) (meth)acrylate, tri(ethylene glycol) (meth)acrylate, tetra(ethylene glycol) (meth)acrylate, poly(ethylene glycol) (meth)acrylate having a number average molecular weight of up to 1500, poly(ethylene glycol)ethyl (meth)acrylamide having a number average molecular weight of up to 1500, and combinations thereof.

14. The hydrogel ocular insert of any one of embodiments 5 to 13, wherein said at least one hydrophilic vinylic monomer comprises a vinylic monomer selected from the group consisting of N-2-aminoethyl (meth)acrylamide, N-2-methylaminoethyl (meth)acrylamide, N-2-ethylaminoethyl (meth)acrylamide, N-2-dimethylaminoethyl (meth)acrylamide, N-3-aminopropyl (meth)acrylamide, N-3-methylaminopropyl (meth)acrylamide, N-3-dimethylaminopropyl (meth)acrylamide, 2-aminoethyl (meth)acrylate, 2-methylaminoethyl (meth)acrylate, 2-ethylaminoethyl (meth)acrylate, 3-aminopropyl (meth)acrylate, 3-methylaminopropyl (meth)acrylate, 3-ethylaminopropyl (meth)acrylate, 3-amino-2-hydroxypropyl (meth)acrylate, trimethylammonium 2-hydroxy propyl (meth)acrylate hydrochloride, dimethylaminoethyl (meth)acrylate, and combinations thereof.

15. The hydrogel ocular insert of any one of embodiments 5 to 14, wherein said at least one hydrophilic vinylic monomer comprises a vinylic monomer selected from the group consisting of 2-(meth)acrylamidoglycolic acid, (meth)acrylic acid, ethylacrylic acid, propylacrylic acid, 3-(meth)acrylamidopropionic acid, 4-(meth)acrylamidobutanoic acid, 5-(meth)acrylamidopentanoic acid, 3-(meth)acryloyloxypropanoic acid, 4-(meth)acryloyloxybutanoic acid, 5-(meth)acryloyloxypentanoic acid, and combinations thereof.

16. The hydrogel ocular insert of any one of embodiments 5 to 15, wherein said at least one hydrophilic vinylic monomer comprises a vinylic monomer selected from the group consisting of N-vinylpyrrolidone (aka, N-vinyl-2-pyrrolidone), N-vinyl-3-methyl-2-pyrrolidone, N-vinyl-4-methyl-2-pyrrolidone, N-vinyl-5-methyl-2-pyrrolidone, N-vinyl-6-methyl-2-pyrrolidone, N-vinyl-3-ethyl-2-pyrrolidone, N-vinyl-4,5-dimethyl-2-pyrrolidone, N-vinyl-5,5-dimethyl-2-pyrrolidone, N-vinyl-3,3,5-trimethyl-2-pyrrolidone, N-vinyl piperidone (aka, N-vinyl-2-piperidone), N-vinyl-3-methyl-2-piperidone, N-vinyl-4-methyl-2-piperidone, N-vinyl-5-methyl-2-piperidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl caprolactam (aka, N-vinyl-2-caprolactam), N-vinyl-3-methyl-2-caprolactam, N-vinyl-4-methyl-2-caprolactam, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, N-vinyl-N-methyl acetamide, N-vinyl formamide, N-vinyl acetamide, N-vinyl isopropylamide, N-vinyl-N-ethyl acetamide, N-vinyl-N-ethyl formamide, and mixtures thereof. Preferably, the N-vinyl amide monomer is N-vinylpyrrolidone, N-vinyl-N-methyl acetamide, or combinations thereof.
17. The hydrogel ocular insert of any one of embodiments 5 to 16, wherein said at least one hydrophilic vinylic monomer comprises a vinylic monomer selected from the group consisting of 1-methyl-3-methylene-2-pyrrolidone, 1-ethyl-3-methylene-2-pyrrolidone, 1-methyl-5-methylene-2-pyrrolidone, 1-ethyl-5-methylene-2-pyrrolidone, 5-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, 1-n-butyl-3-methylene-2-pyrrolidone, 1-tert-butyl-3-methylene-2-pyrrolidone, and combinations thereof.
18. The hydrogel ocular insert of any one of embodiments 5 to 17, wherein said at least one hydrophilic vinylic monomer comprises a vinylic monomer selected from the group consisting of ethylene glycol methyl ether (meth)acrylate, di(ethylene glycol) methyl ether (meth)acrylate, tri(ethylene glycol) methyl ether (meth)acrylate, tetra(ethylene glycol) methyl ether (meth)acrylate, $C_1$-$C_4$-alkoxy poly(ethylene glycol) (meth)acrylate having a weight average molecular weight of up to 1500, methoxy-poly(ethylene glycol)ethyl (meth)acrylamide having a number average molecular weight of up to 1500, and combinations thereof.
19. The hydrogel ocular insert of any one of embodiments 5 to 18, wherein said at least one hydrophilic vinylic monomer comprises a vinylic monomer selected from the group consisting of ethylene glycol monovinyl ether, di(ethylene glycol) monovinyl ether, tri(ethylene glycol) monovinyl ether, tetra(ethylene glycol) monovinyl ether, poly(ethylene glycol) monovinyl ether, ethylene glycol methyl vinyl ether, di(ethylene glycol) methyl vinyl ether, tri(ethylene glycol) methyl vinyl ether, tetra(ethylene glycol) methyl vinyl ether, poly(ethylene glycol) methyl vinyl ether, and combinations thereof.
20. The hydrogel ocular insert of any one of embodiments 5 to 19, wherein said at least one hydrophilic vinylic monomer comprises a vinylic monomer selected from the group consisting of allyl alcohol, ethylene glycol monoallyl ether, di(ethylene glycol) monoallyl ether, tri(ethylene glycol) monoallyl ether, tetra(ethylene glycol) monoallyl ether, poly(ethylene glycol) monoallyl ether, ethylene glycol methyl allyl ether, di(ethylene glycol) methyl allyl ether, tri(ethylene glycol) methyl allyl ether, tetra(ethylene glycol) methyl allyl ether, poly(ethylene glycol) methyl allyl ether, and combinations thereof.
21. The hydrogel ocular insert of any one of embodiments 1 to 11, wherein said at least one arylborono-containing hydrophilic copolymer comprises (a) from about 0.1% to about 25% by mole of the arylborono-containing repeating units, (b) from about 55% to about 98.9% by mole of repeating units of at least one phosphorylcholine-containing vinylic monomer, and (c) from about 1% by mole to about 20% by mole of acrylic monomeric units of at least one acrylic monomer having 3 to 16 carbon atoms, provided that the sum of the mole percentages of components (a), (b) and (c) and other components not listed above is 100%.
22. The hydrogel ocular insert of any one of embodiments 1 to 11, wherein said at least one arylborono-containing hydrophilic copolymer comprises (a) from about 1% to about 20% by mole of the arylborono-containing repeating units, (b) from about 60% to about 97% by mole of repeating units of at least one phosphorylcholine-containing vinylic monomer, and (c) from about 2% to about 20% by mole of acrylic monomeric units of at least one acrylic monomer having 3 to 16 carbon atoms, provided that the sum of the mole percentages of components (a), (b) and (c) and other components not listed above is 100%.
23. The hydrogel ocular insert of any one of embodiments 1 to 11, wherein said at least one arylborono-containing hydrophilic copolymer comprises (a) from about 2% to about 18% by mole of the arylborono-containing repeating units, (b) from about 70% to about 95% by mole of repeating units of at least one phosphorylcholine-containing vinylic monomer, and (c) from about 3% to about 15% by mole of acrylic monomeric units of at least one acrylic monomer having 3 to 16 carbon atoms, provided that the sum of the mole percentages of components (a), (b) and (c) and other components not listed above is 100%.
24. The hydrogel ocular insert of any one of embodiments 21 to 23, wherein said at least one acrylic monomer has 3 to 14 carbon atoms.
25. The hydrogel ocular insert of any one of embodiments 21 to 23, wherein said at least one acrylic monomer has 3 to 12 carbon atoms.
26. The hydrogel ocular insert of any one of embodiments 21 to 23, wherein said at least one acrylic monomer has 3 to 10 carbon atoms.
27. The hydrogel ocular insert of any one of embodiments 21 to 23, wherein said at least one acrylic monomer is selected from the group consisting of a $C_1$-$C_{12}$ alkyl (meth)acrylate, a hydroxy-substituted $C_2$-$C_{12}$ alkyl (meth)acrylate, a carboxy-substituted $C_2$-$C_{12}$ alkyl (meth)acrylate, an $NH_2$-substituted $C_2$-$C_{12}$ alkyl (meth)acrylate, a methylamino-substituted $C_2$-$C_{12}$ alkyl (meth)acrylate, a dimethylamino-substituted $C_2$-$C_{12}$ alkyl (meth)acrylate, an ethylamino-substituted $C_2$-$C_{10}$ alkyl (meth)acrylate, a diethylamino-substituted $C_2$-$C_8$ alkyl (meth)acrylate, a $C_2$-$C_{12}$ alkyl (meth)acrylamide, a hydroxy-substituted $C_2$-$C_{12}$ alkyl (meth)acrylamide, a carboxy-substituted $C_2$-$C_{12}$ alkyl (meth)acrylaide, an $NH_2$-substituted $C_2$-$C_{12}$ alkyl (meth)acrylamide, a methylamino-substituted $C_2$-$C_{12}$ alkyl (meth)acrylamide, a dimethylamino-substituted $C_2$-$C_{12}$ alkyl (meth)acrylamide, an ethylamino-substituted $C_2$-$C_{10}$ alkyl (meth)acrylamide, a diethylamino-substituted $C_2$-$C_8$ alkyl (meth)acrylamide, ethylene glycol (meth)acrylate, di(ethylene glycol) (meth)acrylate, tri(ethylene glycol) (meth)acrylate, tetra(ethylene glycol) (meth)acrylate, ethylene glycol methyl ether (meth)acrylate, di(ethylene glycol) methyl ether (meth)acrylate, tri(ethylene glycol) methyl ether (meth)acrylate, tetra(ethylene glycol) methyl ether (meth)acrylate, and combinations thereof.
28. The hydrogel ocular insert of any one of embodiments 21 to 23, wherein said at least one acrylic monomer is n-butyl (meth)acrylate and/or di(ethylene glycol) methyl ether (meth)acrylate.
29. The hydrogel ocular insert of any one of embodiments 11 and 21 to 28, wherein the phosphorylcholine-containing vinylic monomer is selected from the group consisting of (meth)acryloyloxyethyl phosphorylcholine, (meth)acryloyloxypropyl phosphorylcholine, 4-((meth)acryloyloxy)butyl-2'-(trimethylammonio)

ethylphosphate, 2-[(meth)acryloylamino]ethyl-2'-(trimethylammonio)-ethylphosphate, 3-[(meth)acryloylamino]propyl-2'-(trimethylammonio) ethylphosphate, 4-[(meth)acryloylamino]butyl-2'-(trimethylammonio)ethylphosphate, 5-((meth) acryloyloxy)pentyl-2'-(trimethylammonio)ethyl phosphate, 6-((meth)acryloyloxy)hexyl-2'-(trimethylammonio)-ethylphosphate, 2-((meth)acryloyloxy) ethyl-2'-(triethylammonio)ethylphosphate, 2-((meth) acryloyloxy)ethyl-2'-(tripropylammonio) ethylphosphate, 2-((meth)acryloyloxy)ethyl-2'-(tributylammonio)ethylphosphate, 2-((meth) acryloyloxy)propyl-2'-(trimethylammonio)-ethylphosphate, 2-((meth)acryloyloxy)butyl-2'-(trimethylammonio)ethylphosphate, 2-((meth) acryloyloxy)pentyl-2'-(trimethylammonio) ethylphosphate, 2-((meth)acryloyloxy)hexyl-2'-(trimethylammonio)ethyl phosphate, 2-(vinyloxy) ethyl-2'-(trimethylammonio)ethylphosphate, 2-(allyloxy)ethyl-2'-(trimethylammonio)ethylphosphate, 2-(vinyloxycarbonyl)ethyl-2'-(trimethylammonio)ethyl phosphate, 2-(allyloxycarbonyl)ethyl-2'-(trimethylammonio)-ethylphosphate, 2-(vinylcarbonylamino)ethyl-2'-(trimethylammonio) ethylphosphate, 2-(allyloxycarbonylamino)ethyl-2'-(trimethylammonio)ethyl phosphate, 2-(butenoyloxy) ethyl-2'-(trimethylammonio)ethylphosphate, and combinations thereof.

30. The hydrogel ocular insert of any one of embodiments 1 to 20, wherein the arylborono-containing hydrophilic copolymer comprises (a) from about 0.1% by mole to about 25% by mole of the arylborono-containing repeating units and (b) from about 75% by mole to about 99.9% by mole of repeating units of at least one hydrophilic vinylic monomer, provided that the sum of the mole percentages of components (a) and (b) and other components not listed above is 100%.

31. The hydrogel ocular insert of any one of embodiments 1 to 20, wherein the arylborono-containing hydrophilic copolymer comprises (a) from about 0.1% by mole to about 25% by mole of the arylborono-containing repeating units and (b) from about 80% to about 99% by mole of the repeating units of said at least one hydrophilic vinylic monomer, provided that the sum of the mole percentages of components (a) and (b) and other components not listed above is 100%.

32. The hydrogel ocular insert of any one of embodiments 1 to 20, wherein the arylborono-containing hydrophilic copolymer comprises (a) from about 0.1% by mole to about 25% by mole of the arylborono-containing repeating units and (b) from about 80% to about 98% by mole of repeating units of at least one hydrophilic vinylic monomer, provided that the sum of the mole percentages of components (a) and (b) and other components not listed above is 100%.

33. The hydrogel ocular insert of any one of embodiments 1 to 20, wherein the arylborono-containing hydrophilic copolymer comprises (a) from about 0.1% by mole to about 25% by mole of the arylborono-containing repeating units and (b) from about 82% to about 97% by mole of repeating units of at least one hydrophilic vinylic monomer, provided that the sum of the mole percentages of components (a) and (b) and other components not listed above is 100%.

34. The hydrogel ocular insert of any one of embodiments 1 to 33, wherein the arylborono groups independent of one another have a pKa of from about 6.8 to 9.2.

35. The hydrogel ocular insert of any one of embodiments 1 to 33, wherein the arylborono groups independent of one another have a pKa of from about 7.0 to about 9.0.

36. The hydrogel ocular insert of any one of embodiments 1 to 33, wherein the arylborono groups independent of one another have a pKa of from about 7.2 to about 8.8.

37. The hydrogel ocular insert of any one of embodiments 1 to 33, wherein the arylborono groups independent of one another have a pKa of from about 7.4 to about 8.6.

38. The hydrogel ocular insert of any one of embodiments 1 to 37, wherein said at least one arylborono-containing hydrophilic copolymer has a number average molecular weight of from about 5,000 Daltons to 500,000 Daltons.

39. The hydrogel ocular insert of any one of embodiments 1 to 37, wherein said at least one arylborono-containing hydrophilic copolymer has a number average molecular weight of from about 5,000 Daltons to about 400,000 Daltons.

40. The hydrogel ocular insert of any one of embodiments 1 to 37, wherein said at least one arylborono-containing hydrophilic copolymer has a number average molecular weight of from about 5,000 Daltons to about 250,000 Daltons.

41. The hydrogel ocular insert of any one of embodiments 1 to 40, wherein said at least one mucoadhesive polymer comprises a galactomannan polymer.

42. The hydrogel ocular insert of embodiment 41, wherein the galactomannan polymer is a galactomannan.

43. The hydrogel ocular insert of embodiment 42, wherein the galactomannan has a ratio of D-galactose to D-mannose of from about 1:2 to 1:4.

44. The hydrogel ocular insert of any one of embodiments 41 to 43, wherein the galactomannan is a guar.

45. The hydrogel ocular insert of any one of embodiments 1 to 44, wherein said at least one mucoadhesive polymer comprises a chemically-modified galactomannan.

46. The hydrogel ocular insert of embodiment 45, wherein the chemically-modified galactomannan is selected from the group consisting of Hydroxyethyl guar, hydroxypropyl guar, methyl guar, ethyl guar, propyl guar, carboxymethyl guar, carboxymethylhydroxypropyl guar, hydroxypropyltrimonium chloride guar, and combinations thereof.

47. The hydrogel ocular insert of embodiment 45, wherein the chemically-modified galactomannan is hydroxypropyl guar.

48. The hydrogel ocular insert of any one of embodiments 1 to 47, wherein said at least one mucoadhesive polymer comprises dextran.

49. The hydrogel ocular insert of any one of embodiments 1 to 48, wherein said at least one mucoadhesive polymer comprises mannan.

50. The hydrogel ocular insert of any one of embodiments 1 to 49, wherein said at least one mucoadhesive polymer comprises hyaluronic acid.

51. The hydrogel ocular insert of any one of embodiments 1 to 50, wherein said at least one mucoadhesive polymer comprises polyvinyl alcohol.

52. The hydrogel ocular insert of any one of embodiments 1 to 51, wherein said at least one mucoadhesive polymer is present in an amount of from about 50% to about 99% by weight relative to the dry weight of the hydrogel ocular insert.

53. The hydrogel ocular insert of any one of embodiments 1 to 51, wherein said at least one mucoadhesive polymer is present in an amount of from about 60% to about 99% by weight by weight relative to the dry weight of the hydrogel ocular insert.
54. The hydrogel ocular insert of any one of embodiments 1 to 51, wherein said at least one mucoadhesive polymer is present in an amount of from about 70% to about 98% by weight relative to the dry weight of the hydrogel ocular insert.
55. The hydrogel ocular insert of any one of embodiments 1 to 51, wherein said at least one mucoadhesive polymer is present in an amount of from about 80% to about 98% by weight relative to the dry weight of the hydrogel ocular insert.
56. The hydrogel ocular insert of any one of embodiments 1 to 55, wherein the hydrogel ocular insert is hydrolytically stable in an aqueous solution at a pH of from about 7.5 to 9.5 and has an equilibrium water content of from about 10% to about 70% by weight (at room temperature, about 22° C. to 28° C.), when being fully hydrated.
57. The hydrogel ocular insert of any one of embodiments 1 to 55, wherein the hydrogel ocular insert is hydrolytically stable in an aqueous solution at a pH of from about 7.5 to 9.5 and has an equilibrium water content of from about 20% to about 65% by weight (at room temperature, about 22° C. to 28° C.), when being fully hydrated.
58. The hydrogel ocular insert of any one of embodiments 1 to 55, wherein the hydrogel ocular insert is hydrolytically stable in an aqueous solution at a pH of from about 7.5 to 9.5 and has an equilibrium water content of from about 25% to about 60% by weight (at room temperature, about 22° C. to 28° C.), when being fully hydrated.
59. The hydrogel ocular insert of any one of embodiments 1 to 55, wherein the hydrogel ocular insert is hydrolytically stable in an aqueous solution at a pH of from about 7.5 to 9.5 and has an equilibrium water content of from about 30% to about 55% by weight (at room temperature, about 22° C. to 28° C.), when being fully hydrated.
60. The hydrogel ocular insert of any one of embodiments 1 to 59, wherein the hydrogel ocular insert has a shape having a maximum size in any single dimension of 5-6 mm.
61. The hydrogel ocular insert of embodiment 60, wherein the hydrogel ocular insert has a shape of a rod, a sphere, an oval, a ring, a square, a rectangle, a triangle, or an irregular shape.
62. The hydrogel ocular insert of any one of embodiments 1 to 61, wherein the hydrogel ocular insert has a thickness of about 50 to about 400 μm.
63. The hydrogel ocular insert of any one of embodiments 1 to 61, wherein the hydrogel ocular insert has a thickness of about 60 to about 300 μm.
64. The hydrogel ocular insert of any one of embodiments 1 to 61, wherein the hydrogel ocular insert has a thickness of about 60 to about 250 μm.
65. The hydrogel ocular insert of any one of embodiments 1 to 64, wherein the hydrogel ocular insert has an on-eye dissolution time of at least 3 hours.
66. The hydrogel ocular insert of any one of embodiments 1 to 64, wherein the hydrogel ocular insert has an on-eye dissolution time of at least 4 hours.
67. The hydrogel ocular insert of any one of embodiments 1 to 64, wherein the hydrogel ocular insert has an on-eye dissolution time of from about 4 to 24 hours.
68. The hydrogel ocular insert of any one of embodiments 1 to 67, wherein the hydrogel ocular insert has a layered structure and comprises a first hydrogel layer sandwiched between two second hydrogel layers, wherein the first hydrogel layer has a first crosslinking density of first crosslinks and the second hydrogel layers have a second crosslinking density of second crosslinks, wherein the first crosslinking density is higher than the second crosslinking density and/or the first crosslinks are more stable than the second crosslinks (i.e., hydrolyzing more slowly than the second crosslinks in the tear of the eye).
69. The hydrogel ocular insert of any one of embodiments 1 to 68, wherein the hydrogel ocular insert comprises one or more additional pharmaceutical active agents.
70. The hydrogel ocular insert of embodiment 69, wherein said one or more additional pharmaceutical active agents are selected from the group consisting of ocular lubricants, anti-redness relievers (such as brimonidine tartrate, tetrahydrozoline, naphazoline), cooling agents (such as menthol), steroids and nonsteroidal anti-inflammatory agents to relieve ocular pain and inflammation, antibiotics, anti-histamines (such as olopatadine), anti-virals, antibiotics and anti-bacterials for infectious conjunctivitis, anti-muscarinics (such as atropine and derivatives thereof) for myopia treatment, and glaucoma drug delivery (such as prostaglandin and prostaglandin analogs such as travoprost), and therapeutically suitable combinations thereof.
71. The hydrogel ocular insert of any one of embodiments 1 to 70, wherein the hydrogel ocular insert is stored in a packaging aqueous solution in a sealed and sterilized package.
72. The hydrogel ocular insert of embodiment 71, wherein the packaging aqueous solution has a pH of from about 7.5 to about 9.0 and a tonicity of from about 200 to about 450 milliosmol (mOsm).
73. The hydrogel ocular insert of embodiment 71 or 72, wherein the packaging aqueous solution comprises a surfactant, an antibacterial agent, a preservative, a lubricant (e.g., cellulose derivatives, polyvinyl alcohol, polyvinylpyrrolidone), or a combination thereof.
74. A method for producing a hydrogel ocular insert of any one of embodiments 1 to 73, comprising the step of: curing a reactive composition to form a hydrogel which is in a form of the ocular insert or is machined into the form of the ocular insert, wherein the reactive composition comprises said at least one arylborono-containing hydrophilic copolymer and said at least one mucoadhesive polymer both dissolved in a solvent.
75. The method of embodiment 74, wherein the solvent is water or a mixture of water with one or more organic solvents miscible with water.
76. The method of embodiment 74, wherein the solvent is an organic solvent or a mixture of at two or more organic solvents.
77. The method of any one of embodiments 74 to 76, wherein the step of curing is carried out by mixing one first solution of said at least one arylborono-containing hydrophilic copolymer with one second solution of said at least one mucoadhesive hydrophilic polymer in a mold to obtain a reactive composition having a pH at which said at least one arylborono-containing hydrophilic copolymer and said at least one mucoadhesive polymer are crosslinked through crosslinks each formed between one arylborono group of the arylborono-containing hydrophilic copolymer and one 1,2- diol, 1,3-diol, α-hydroxycarboxylic acid, or 8-hydroxycarboxylic acid moiety of the mucoadhesive polymer.

78. The method of any one of embodiments 74 to 76, wherein the step of curing is carried out by increasing the pH of a third solution containing a mixture of said at least one arylborono-containing hydrophilic copolymer and said at least one mucoadhesive hydrophilic polymer in a mold to a pH at which said at least one arylborono-containing hydrophilic copolymer and said at least one mucoadhesive polymer are crosslinked through crosslinks each formed between one arylborono group of the arylborono-containing hydrophilic copolymer and one 1,2-diol, 1,3-diol, α-hydroxycarboxylic acid, or 8-hydroxycarboxylic acid moiety of the mucoadhesive polymer.

79. The method of embodiment 78, wherein the increasing of pH is carried out by adding a base solution having a pH of about 10.0 or higher.

80. The method of any one of embodiments 74 to 79, wherein the step of curing is carried according to reactive injection molding technique.

81. The method of any one of embodiments 74 to 80, further comprising the steps of contacting the hydrogel with an aqueous solution having a pH for stabilizing the hydrogel and fully hydrating the hydrogel; and sterilizing the hydrogel.

82. The method of any one of embodiments 74 to 81, further comprising steps of placing the hydrogel insert in a packaging aqueous solution in a package; sealing the package; and sterilizing the sealed package with the hydrogel ocular insert immersed in the packaging aqueous solution therein.

83. A method for using of a hydrogel ocular insert of any one of embodiments 1 to 73 for treating a disease or disorder of an eye of a subject, comprising administering the hydrogel ocular insert into the eye.

The previous disclosure will enable one having ordinary skill in the art to practice the invention. Various modifications, variations, and combinations can be made to the various embodiment described herein. In order to better enable the reader to understand specific embodiments and the advantages thereof, reference to the following examples is suggested. It is intended that the specification and examples be considered as exemplary.

Chemicals

The following abbreviations are used in the following examples: NVP represents N-vinylpyrrolidone; VPBA represents 4-vinylphenylboronic acid; PVA represents polyvinylalcohol; PVP represents polyvinylpyrrolidone; HA represents hyaluronic acid; HP-guar represents hydroxypropyl guar; MPC represent 2-methacryloyloxyethyl phosphorylcholine; PBS represents a phosphate-buffered saline which has a pH of 7.2±0.2 at 25° C. and contains about 0.044 wt. % $NaH_2PO_4 \cdot H_2O$, about 0.388 wt. % $Na_2HPO_4 \cdot 2H_2O$, and about 0.79 wt. % NaCl and; wt. % represents weight percent; TAA represents tert-amyl alcohol; PrOH represents 1-propanol; IPA represents isopropanol; $PEG_{200}MA$ represents polyethylene glycol monomethacrylate having a number average molecular weight, Mn, of 200 Daltons; $PEG_{300}MA$ represents polyethylene glycol monomethacrylate having a number average molecular weight, Mn, of 300 Daltons; $PEG_{950}MA$ represents polyethylene glycol monomethacrylate having a number average molecular weight, Mn, of 950 Daltons; DMA represents N,N-dimethylacrylamide; BMA represents n-butyl methacrylate; AAPH represent 2,2'-azobis-(2-amidinopropane dihydrochloride; DI water represents deionized water; βME represents β-mercaptoethanol; HPMC represents hydroxypropyl methylcellulose; PEG400 represents polyethylene glycol having a number average molecular weight of 400 Daltons; VAZO 64 represents 2,2'-dimethyl-2,2'azodipropiononitrile.

Example 1

This example illustrates how to prepare arylborono-containing hydrophilic copolymers by copolymerizing a polymerizable composition which comprises (a) an arylborono-containing vinylic monomer (VPBA) and (b) an hydrophilic vinylic monomer (NVP or $PEG_{200}MA$). The molecular weights of the resultant arylborono-containing hydrophilic copolymers are determined by GPC/RI method with Pullulan standards (Ready Cal-Kit Pullulan high (180-1.22M MP): Part No. PSS-Pulkitrih) for determining molecular weight of VPB Copolymer (GPC Column: Waters Ultra-Hydrogel Linear 300×7.8 mm column; Oven Temperature: 30° C.; RI-Detector: room temperature; Eluent: aqueous solution of 0.2M sodium nitrate and 0.02 w/w % sodium azide; flow rate: 0.5 mL/min; Sample Concentration: 3 g/L; Injection Volume: 100 μl).

Synthesis of NVP-VPBA Copolymer

In a 100 ml round bottom flask, 1-Phenylvinylboronic acid 0.32 g, NVP 4.47 g and 0.047 g of Vazo 64 are added. A Nitrogen inlet is connected to the flask, as well as a water condenser. The flask is set in oil bath with magnetic stir and heated at 75° C. for 5 hours. After the reaction mixture cool down to room temperature, it is transferred to 20 ml glass vial. Nitrogen is blown into the liquid via a needle overnight and an amber color very sticky liquid is obtained. An aqueous solution of the obtained product (2% by weight) is completely clear. Aqueous phase GPC test shows number average molecular weight of 367 K Da with polydispersity of 2.6.

Synthesis of Binary Copolymer poly($PEG_{200}MA$-co-VPBA)

About 1.133 g of VPBA is dissolved in 25.0 g PrOH to obtain a VPBA solution which is introduced, through a syringe equipped with a 5 μm nylon filter, into a 500 mL reactor equipped with $N_2$ inlet, overhead stirrer, thermocouple, condenser, and bubbler. About 18.88 g of $PEG_{200}MA$ is dissolved in 20.0 g DI water, poured into the reactor and rinsed in with an additional 2×20.0 g DI water. About 00693 g of AAPH is dissolved in 5.0 g DI water, poured into reactor and rinsed in with an additional 2×5.0 g DI water, followed by 15.0 g DI water and 65.0 g PrOH. About 3.65 mL of mercaptoethanol (βME) solution (0.274 g βME in 100 mL of DI water) is added with a micropipette.

The reaction solution is purged with nitrogen (200 mL/minute) for 30 minutes at 20° C. while stirring at 150 rpm. Nitrogen flow is reduced to a blanket and the copolymerization solution is heated according to the following schedule: taking two hours to reach 61° C.; maintaining at 61° C. for about 8 hours; and taking 2 hours to cool down to 20° C.

Example 2

This example illustrates how to prepare arylborono-containing hydrophilic copolymers by copolymerizing a polymerizable composition which comprises (a) an arylborono-containing vinylic monomer (VPBA) and (b) two hydrophilic vinylic monomers (MPC or $PEG_{200}MA$). The molecular weights of the resultant arylborono-containing hydrophilic copolymers are determined by GPC/RI method as described in Example 1.

Synthesis of Terpolymer—Poly(PEG$_{200}$MA-co-MPC-co-VPBA) terpolymer

About 1.011 g of VPBA is dissolved in 25.0 g PrOH to obtain a VPBA solution which is introduced, through a syringe equipped with a 5 μm nylon filter, into a 500 mL reactor equipped with N$_2$ inlet, overhead stirrer, thermocouple, condenser, and bubbler. About 12.278 g of PEG$_{200}$MA is dissolved in 20.0 g DI water, poured into the reactor and rinsed in with an additional 15.0 g DI water. About 6.714 g of MPC is dissolved in 20.0 g DI water, poured into the reactor and rinsed in with an additional 15.0 g DI water. About 00693 g of AAPH is dissolved in 5.0 g deionized water, poured into reactor and rinsed in with an additional 2×5.0 g deionized water, followed by 5.0 g deionized water and 65.0 g n-propanol. About 3.65 mL of mercaptoethanol (βME) solution (0.274 g βME in 100 mL of DI water) is added with a micropipette.

The reaction solution is purged with nitrogen (200 mL/minute) for 30 minutes at 20° C. while stirring at 150 rpm. Nitrogen flow is reduced to a blanket and the copolymerization solution is heated according to the following schedule: taking two hours to reach 61° C.; maintaining at 61° C. for about 8 hours; and taking 2 hours to cool down to 20° C.

Various copolymers (binary or ternary) are prepared according to the procedures described above except different amounts and types of vinylic monomers as indicated in Table 1.

Poly(MPC$_{0.4}$-co-NVP$_{0.5}$-co-VPBA$_{0.1}$)

In a 20 ml vial, add 1.18 g (4 mmol) of MPC, 0.556 g (5 mmol) of NVP and 0.148 g (1 mmol) of VPBA and 10 ml Ethanol, vazo64 1.64 mg (0.01 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum.

Poly(MPC$_{0.6}$-co-BMA$_{0.3}$-co-VPBA$_{0.1}$)

In a 20 ml vial, add 1.77 g (6 mmol) of MPC, 0.426 g (3 mmol) of BMA and 0.148 g (1 mmol) of VPBA and 10 ml Ethanol, vazo64 1.64 mg (0.01 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 150 KDa.

Poly(MPC$_{0.8}$-co-BMA$_{0.1}$-co-VPBA$_{0.1}$)

In a 20 ml vial, add 2.36 g (8 mmol) of MPC, 0.142 g (1 mmol) of BMA and 0.148 g (1 mmol) of VPBA and 10 ml Ethanol, vazo64 1.64 mg (0.01 mmol) are added. Nitrogen

TABLE 1

| | Component (mole %) | | | | | | [BA]* | Mn | Mw | |
|---|---|---|---|---|---|---|---|---|---|---|
| | VPBA | PEG$_{300}$MA | PEG$_{950}$MA | PEG$_{200}$MA | DMA | MPC | (meq/g) | (KD) | (KD) | PDI |
| Copolymer 1 | 5.0 | 0 | 0 | 0 | 95.0 | 0 | 0.52 | | | |
| Copolymer 2 | 10.0 | 0 | 0 | 0 | 90.0 | 0 | 1.29 | | | |
| Copolymer 3 | 7.5 | 92.5 | 0 | 0 | 0 | 0 | 0.23 | 192 | 341 | 1.8 |
| Terpolymer 1 | 7.5 | 67.5 | 0 | 0 | 0 | 25.0 | 0.22 | 181 | 328 | 1.8 |
| Terpolymer 2 | 7.5 | 0 | 67.5 | 0 | 0 | 25.0 | 0.10 | 152 | 398 | 2.6 |
| Copolymer 4 | 7.5 | 0 | 0 | 92.5 | 0 | 0 | 0.33 | 81 | 132 | 1.6 |
| Terpolymer 3 | 7.5 | 0 | 0 | 67.5 | 0 | 25.0 | 0.32 | 74 | 122 | 1.6 |
| Copolymer 5 | 12.5 | 0 | 0 | 87.5 | 0 | 0 | 0.57 | 112 | 173 | 1.5 |
| Terpolymer 4 | 12.5 | 0 | 0 | 62.5 | 0 | 25.0 | 0.51 | 142 | 229 | 1.6 |

*the concentration (milliequivalents) of boronic acid (BA) groups in a copolymer is determined by titration Example 3

This example illustrates how to prepare arylborono-containing hydrophilic copolymers by copolymerizing a polymerizable composition which comprises (a) an arylborono-containing vinylic monomer (VPBA), (b) one or two hydrophilic vinylic monomers, and (c) optionally a hydrophobic vinylic monomer. The molecular weights of the resultant arylborono-containing hydrophilic copolymers are determined by GPC/RI method as described in Example 1.

Synthesis of Binary and Ternary Copolymers

Poly(MPC$_{0.9}$-co-VPBA$_{0.1}$)

In a 20 ml vial, add 2.66 g (9 mmol) of MPC and 0.148 g (1 mmol) of VPBA and 10 ml Ethanol, vazo 64 1.64 mg (0.01 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum.

gas is gently bubbled into the solution for 5 min to eliminate the oxygen and then the vial is sealed. The polymerization was performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined by GPC/RI method to have a weight average molecular weight, Mw, of 160 KDa.

Poly(MPC$_{0.8}$-co-BMA$_{0.1}$-co-VPBA$_{0.1}$)

In a 40 ml vial, add 4.72 g (16 mmol) of MPC, 0.285 g (2 mmol) of BMA and 0.296 g (2 mmol) of VPBA and 20 ml Ethanol, vazo64 3.2 mg (0.02 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 286 KDa.

Poly(MPC$_{0.8}$-co-BMA$_{0.1}$-co-VPBA$_{0.1}$)

In a 40 ml vial, add 4.72 g (16 mmol) of MPC, 0.285 g (2 mmol) of BMA and 0.296 g (2 mmol) of VPBA and 20 ml Ethanol, vazo64 1.3 mg (0.01 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 386 KDa.

Poly(MPC$_{0.8}$-co-BMA$_{0.1}$-co-VPBA$_{0.1}$)

In a 40 ml vial, add 4.72 g (16 mmol) of MPC, 0.285 g (2 mmol) of BMA and 0.296 g (2 mmol) of VPBA and 10 ml Ethanol, vazo64 3.2 mg (0.02 mmol) are added. Nitrogen gas is gently bubbled into the solution for 5 min to eliminate the oxygen and then the vial is sealed. The polymerization is performed at 60° C. for a 6 hrs. After cooling the vial, the contents are poured into a large amount of a mixture of diethyl ether and chloroform (8/2 by volume) to eliminate any remaining monomer and precipitate the polymer. The precipitate is filtered off using a glass-filter and dried in vacuum. The obtained copolymer is determined to have a weight average molecular weight, Mw, of 688 KDa.

Example 4

This example illustrates how to prepare arylborono-containing hydrophilic copolymers by copolymerizing a polymerizable composition which comprises (a) an arylborono-containing vinylic monomer (VPBA), (b) one or two hydrophilic vinylic monomers, and (c) optionally a hydrophobic vinylic monomer. The molecular weights of the resultant arylborono-containing hydrophilic copolymers are determined by GPC/RI method as described in Example 1.

Synthesis of Binary and Ternary Copolymers

Add 2-methacryloyloxyethyl phosphorylcholine (MPC) (Mw=295.27), 4-vinyl phenyl boronic acid (VPBA, Mw=147.97), and optionally a third monomer (n-butyl methacrylate (BMA, Mw=142.20) or di(ethylene glycol) methyl ether methacrylate (DGMEMA, Mw=188.22), ethanol, and DI water into a 1 L jacketed reactor, in the amounts shown in Table 2. Degas the solution for 30 minutes at a nitrogen flow rate of 250 mL/min. Dissolve Vazo-56 into 20 to 30 g of DI water. Degas the initiator solution for 30 minutes at a nitrogen flow rate of about 50 mL/min. in an addition funnel. Heat the solution in the reactor to 49° C. Add initiator solution and maintain solution temperature for 16 hours.

Purification:

Dilute solution after the reaction to about 10% solids with DI water. Filter solution from synthesis step through a course-fritted filter. Dilute solution to 7.5-5.0% solids for purification by ultrafiltration using a polyether sulfone membrane with 30 kDa molecular weight cutoff. Use 8 to 10 bed volumes of water to remove residual monomer and solvent.

Polymer Characterization:

The boronic acid content of the copolymer is determined by carrying an acid base titration in the presence of mannitol. The results are reported in Table 2.

The weight average molecular weight of the copolymers are determined using GPC with an RI detector and PEG standards. The results are reported in Table 2.

TABLE 2

| Components | Synthesis | | | |
| --- | --- | --- | --- | --- |
| | Copolymer 9A | Copolymer 9B | Copolymer 9C | Copolymer 9D |
| MPC (g) | 66.80 | 59.03 | 158.21 | 71.09 |
| VPBA (g) | 4.187 | 3.696 | 9.908 | 3.956 |
| BMA (g) | 4.023 | — | — | — |
| DGMEMA (g) | — | 4.702 | 12.606 | — |
| Vazo-56 (g) | 0.0768 | 0.0679 | 0.1818 | 0.0729 |
| Ethanol (g) | 212.5 | 191 | 257.1 | 170.0 |
| Water (g) | 212.5 | 191 | 257.1 | 255 |
| Mw (kDa) | 993 | 579 | 2,176 | 1,227 |
| Mn (kDa) | 317 | 148 | 460 | 403 |
| PDI (Mw/Mn) | 3.1 | 4.0 | 4.7 | 3.2 |
| Boronic acid (meq/g) | 0.341 | 0.495 | 0.325 | 0.306 |

Example 5

This example illustrates how to prepare arylborono-containing hydrophilic copolymers by copolymerizing a polymerizable composition which comprises (a) an arylborono-containing vinylic monomer (VPBA), (b) one or two hydrophilic vinylic monomers, and (c) optionally a hydrophobic vinylic monomer. The molecular weights of the resultant arylborono-containing hydrophilic copolymers are determined by GPC/RI method as described in Example 1.

Binary and Ternary Copolymers

Binary and ternary copolymers are synthesized from a reactive composition shown in Table 3, according to the procedures described in Example 4, except that the polymerization reaction is carried out at 52° C. The resultant copolymer are purified and characterized according to the procedures described in Example 4. The results are reported in Table 3.

TABLE 3

| Formulation | 11A | 11B | 11C |
| --- | --- | --- | --- |
| MPC (g) | 55.7 | 52.9 | 54.7 |
| VPBA (g) | 3.49 | 3.30 | 3.43 |
| BMA (g) | 3.35 | — | — |
| DGMEMA (g) | — | — | 4.36 |
| Vazo-56 (g) | 0.064 | 0.060 | 0.063 |
| Ethanol (g) | 218.7 | 218.7 | 218.7 |
| Water (g) | 218.7 | 218.7 | 218.7 |
| Mw (kDa) | 623 | 913 | 705 |
| Boronic acid (meq/g) | 0.344 | 0.304 | 0.327 |

Example 6

Poly(MPC$_{0.8}$-co-BMA$_{0.1}$-co-VPBA$_{0.1}$) (Mw 160 KDa) prepared in Example 3 is used in this Example.

The compositions (Formulations A-E) having a total solid content of 5 mg/ml for preparing ocular inserts are prepared by dissolving hyaluronic acid (HA), hydroxypropyl guar (HP-guar) and polyvinylpyrrolidone (PVP, 40K) in deionized (DI) water (stirred for 16 hours at room temperature) and adding a designed amount of an aqueous solution of VPBA copolymer (i.e., "Poly(MPC$_{008}$-co-BMA$_{0.1}$-co-VPBA$_{0.1}$)") (stirred for 10 min) to have a composition shown in Table 4.

A composition (Formulation F) having a total solid content of 5 mg/ml for preparing ocular inserts are prepared by dissolving 45 weight unit parts of HA, 45 weight unit parts of HP-guar, and 10 weight unit parts of PVP (40K) in deionized (DI) water (stirred for 16 hours at room temperature) and adding 2 weight unit parts of $CaCl_2$.

The prepared compositions each are then poured into glass dishes, dried in oven at 70° C. with airflow for about 20 hours to form film. All films are transparent to semi transparent, with thickness 40-50 µm and are punched into ocular inserts in a form of 6 mm wafers. The obtained ocular inserts are tested for dissolution time in two different liquid media: DI water (pH~4, equivalent to HA/HP-Guar solution in DI water) or a phosphate-buffered saline (PBS, pH~7.2) at 37° C. in a water bath. The results of dissolution tests for ocular inserts made from Formulations A-E are reported in Table 4. For ocular inserts made from Formulation F, they have a dissolution time of 95-100 minutes in DI water (pH~4, equivalent to HA/HP-Guar solution in DI water) or about 4 hours in PBS (pH~7.2).

TABLE 4

| Components | Formulation (weight unit parts) | | | | |
|---|---|---|---|---|---|
|  | A | B | C | D | E |
| HA | 45 | 45 | 45 | 45 | 45 |
| HP-guar | 45 | 45 | 45 | 45 | 45 |
| PVP(40k) | 10 | 10 | 10 | 10 | 10 |
| VPBA Copolymer | 0 | 0.5 | 1 | 2 | 5 |
| Dissolution Time of Ocular Inserts | | | | | |
| in DI water (minutes) | 50-55* | 55-60 | 55-60 | 55-60 | 65-70 |
| in PBS (hour) | 2.5-4.5 | 3.2-4.5 | 4.2-4.8 | 5-6 | 5-6 |

It has been found that the dissolution times of ocular inserts in DI water (pH~4) are quite similar, 50-65 minutes, for ocular inserts made from all formulations with or without the arylborono-containing hydrophilic copolymer, which would function as crosslinkers for crosslinking those mucoadhesive polymer chains via cyclic boronic ester crosslinks (each formed between one phenylboronic acid group and one 1,2- or 2,3-diols) to form 3-dimensional polymer network. It has also been found that the dissolution times of ocular inserts in PBS (pH~7.2) are much longer, 2-6 hours. It has further been found that the dissolution times of ocular inserts in artificial tear fluids (pH~7.2) are similar to what found in PBS (pH~7.2). Compared to ocular inserts made from Formulation A (control), the dissolution times of ocular inserts in PBS (pH~7.2) are increased significantly, increasing from 3.2-4.5 hours to 5-6 hours when the concentration of the arylborono-containing hydrophilic copolymer increased from 0.5 to 5.0 weight unit parts in the formulation for making ocular inserts.

Considering that the pka of 4-vinylphenylboronic acid is about 8.8 (Vancoillie & Hoogenboom, Polym. Chem. 2016, 7: 5484-5495), it is believed that cyclic boronic ester crosslinks would be hydrolyzed too fast at pH~4 (i.e., in DI water) so that the polymer chains making up ocular inserts are practically held together entirely by non-covalent bonds (e.g., hydrogen bonds, etc.), whereas at pH~7.2 (i.e., in PBS) cyclic boronic ester crosslinks would be hydrolyzed at a much slower rate so that the polymer chains making up ocular inserts are held together by covalent bonds (cyclic boronic ester crosslinks) and non-covalent bonds (e.g., hydrogen bonds, etc.).

In a different experiment, the ocular inserts prepared from Formulation E has been placed in a PBS the pH of which has been increased to about 10. It has been found that those ocular inserts are fully hydrated and remain stable in the PBS (pH 10).

All the publications, patents, and patent application publications, which have been cited herein above in this application, are hereby incorporated by reference in their entireties.

What is claimed is:

1. A hydrogel ocular insert,
wherein the hydrogel ocular insert is placed into the cul-de-sac or conjunctival sac of an eye when being used by a patient and is made of a hydrogel material; and
wherein the hydrogel ocular insert is stored in a packaging aqueous solution in a sealed and sterilized package, wherein the packaging aqueous solution has a pH of from about 7.5 to about 9.0,
wherein the hydrogel material is a crosslinked polymeric material which is a crosslinking product of at least one arylborono-containing hydrophilic copolymer including arylborono-containing repeating units each having an arylborono group and at least one mucoadhesive polymer including repeating units each having a moiety selected from the group consisting of 1,2-diol moiety, 1,3-diol moiety, α-hydroxycarboxylic acid moiety, and β-hydroxycarboxylic acid moiety, wherein said at least one arylborono-containing hydrophilic copolymer and said at least one mucoadhesive polymer are crosslinked in the hydrogel material through crosslinks each formed between one of arylborono groups of said at least one arylborono-containing hydrophilic copolymer and one 1,2-diol, 1,3-diol, α-hydroxycarboxylic acid, or β-hydroxycarboxylic acid moiety of said at least one mucoadhesive polymer, and
wherein the hydrogel ocular insert has an on-eye dissolution time of from about 4 to about 24 hours.

2. The hydrogel ocular insert of claim 1, wherein said at least one arylborono-containing hydrophilic copolymer comprises an arylborono-containing vinyl-based copolymer comprising (a) arylborono-containing repeating units of at least one arylborono-containing vinylic monomer and (b) hydrophilic repeating units of at least one hydrophilic vinylic monomer.

3. The hydrogel ocular insert of claim 2, wherein said at least one arylborono-containing vinylic monomer is represented by formula (II)

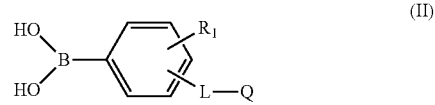

in which: $R_1$ is H, $NO_2$, F, Cl, Br, $CF_3$, $CH_2OH$, or $CH_2NR^oR^o1$; Q is a monovalent radical of

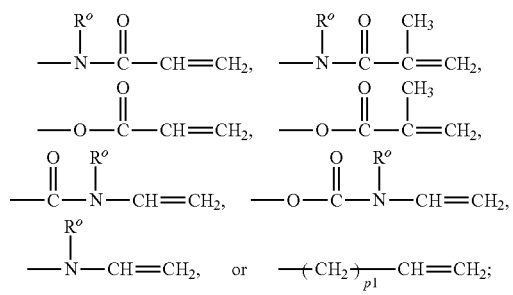

L is a direct bond, a $C_1$-$C_4$ alkylene divalent radical, a divalent radical of

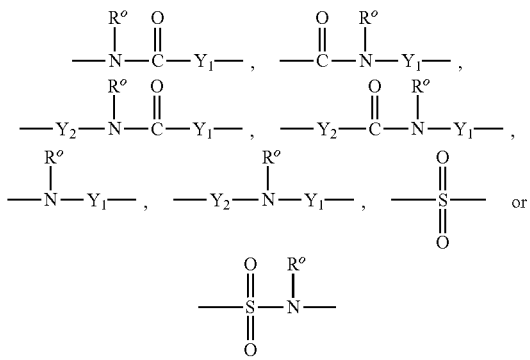

in which $Y_1$ is CH(OH) or a $C_1$-$C_4$ alkylene divalent radical, $Y_2$ is a $C_1$-$C_4$ alkylene divalent radical, p1 is an integer of 0 to 3, and $R^o$ and $R^{o'}$ independent of each other are H or a $C_1$-$C_4$ alkyl.

4. The hydrogel ocular insert of claim 3, wherein said at least one arylborono-containing vinylic monomer is selected from the group consisting of 3-vinylphenylboronic acid, 4-vinylphenylboronic acid, 3-(meth)acrylamidophenylboronic acid, 4-(meth)acrylamidophenyl boronic acid, 3-(meth)acrylamido-5-nitrophenylboronic acid, 4-(meth) acrylamido-5-nitrophenylboronic acid, 4-(meth)acrylamido-3-nitrophenyl-boronic acid, 3-[(meth)acrylamido-$C_2$-$C_5$-alkylaminocarbonyl]-5-nitrophenylboronic acid, 3-[(meth)acryloyloxy-$C_2$-$C_5$-alkylamino-carbonyl]-5-nitrophenyl boronic acid, 3-(meth)acrylamido-6-hydroxymethylphenylboronic acid, 3-(meth)acrylamido-6-dimethylaminomethylphenylboronic acid, 4-(meth)acrylamido-6-hydroxymethylphenyl-boronic acid, 4-(meth)acrylamido-6-dimethylaminomethylphenyl-boronic acid, 4-(1,6-Dioxo-2,5-diaza-7-oxamyl)phenylboronic acid, 4-(N-allylsulfamoyl) phenylboronic acid, 4-(3-butenylsulfonyl)phenylboronic acid, a reaction production of an amino-containing phenylboronic acid derivative with (meth)acrylic acid halide, a reaction product of an amino-containing phenylboronic acid derivative with a carboxy-containing vinylic monomer in the presence of a carbodiimide and N-hydroxysuccinimide, a reaction production of a carboxy-containing phenylboronic acid derivative with an amino-containing vinylic monomer in the presence of a carbodiimide and N-hydroxysuccinimide, and combinations thereof, wherein the carboxy-containing phenylboronic acid derivative is selected from the group consisting of 3-carboxyphenylboronic acid, 4-carboxyphenylboronic acid, 3-boronophenylacetic acid, 4-boronophenylacetic acid, 2-(4-boronophenyl)-2-methylpropanoic acid, 3-(4-boronophenyl)propanoic acid, 3-(3-boronophenyl)propanoic acid, 5-(3-boronophenyl)-pentanoic acid, 5-(4-boronophenyl)pentanoic acid, 4-(2-carboxyethyl)-3-nitrophenyl-boronic acid, 3-carboxy-5-nitrophenylboronic acid, 4-carboxy-3-chlorophenylboronic acid, 3-carboxy-4-fluorophenylbornic acid, 3-(3-carboxypropyonylamino)phenylboronic acid, 3-amino-3-(4-boronophenyl)propanoic acid, and combinations thereof, wherein the amino-containing phenylboronic acid derivative is selected from the group consisting of 3-aminophenylboronic acid, 4-aminophenylboronic acid, 4-amino-3-nitrophenylboronic acid, 3-amino-6-hydroxymethylphenylboronic acid, 3-amino-6-(dimethylaminomethyl)phenylboronic acid, 4-amino-2-hydroxymethylphenylboronic acid, 4-amino-2-(dimethylaminomethyl)phenylboronic acid, 3-amino-4-fluorophenyl-boronic acid, 4-(aminomethyl)-5-nitrophenylboronic acid, 3-(aminomethyl)-phenyl-boronic acid, 3-amino-5-nitrophenylboronic acid, 3-amino-3-(4-boronophenyl)propanoic acid, and combinations thereof, wherein the carboxyl-containing vinylic monomer is selected from the group consisting of 2-acrylamidoglycolic acid, 3-acrylamidopropionic acid, 4-acrylamidobutanoic acid, 5-acrylamidopentanoic acid, 3-acryloyloxypropanoic acid, 4-acryloyloxybutanoic acid, 5-acryloyloxypentanoic acid, and combinations thereof, wherein the amino-containing vinylic monomers is selected from the group consisting of amino-$C_2$-$C_4$ alkyl (meth)acrylate, $C_1$-$C_3$ alkylamino-$C_2$-$C_4$ alkyl (meth)acrylate, amino-$C_2$-$C_4$ alkyl (meth)acrylamide, $C_1$-$C_3$ alkylamino-$C_2$-$C_4$ alkyl (meth)acrylamide, vinylamine, allylamine, and combinations thereof.

5. The hydrogel ocular insert of claim 1, wherein said at least one arylborono-containing hydrophilic copolymer comprises (a) from about 0.1% to about 25% by mole of the arylborono-containing repeating units, (b) from about 55% to about 98.9% by mole of repeating units of at least one phosphorylcholine-containing vinylic monomer, and (c) from about 1% by mole to about 20% by mole of acrylic monomeric units of at least one acrylic monomer having 3 to 16 carbon atoms, provided that the sum of the mole percentages of components (a), (b) and (c) and other components not listed above is 100%.

6. The hydrogel ocular insert of claim 5, wherein said at least one acrylic monomer is selected from the group consisting of a $C_1$-$C_{12}$ alkyl (meth)acrylate, a hydroxy-substituted $C_2$-$C_{12}$ alkyl (meth)acrylate, a carboxy-substituted $C_2$-$C_{12}$ alkyl (meth)acrylate, an $NH_2$ substituted $C_2$-$C_{12}$ alkyl (meth)acrylate, a methylamino-substituted $C_2$-$C_{12}$ alkyl (meth)acrylate, a dimethylamino-substituted $C_2$-$C_{12}$ alkyl (meth)acrylate, an ethylamino-substituted $C_2$-$C_{10}$ alkyl (meth)acrylate, a diethylamino-substituted $C_2$-$C_8$ alkyl (meth)acrylate, a $C_2$-$C_{12}$ alkyl (meth)acrylamide, a hydroxy-substituted $C_2$-$C_{12}$ alkyl (meth)acrylamide, a carboxy-substituted $C_2$-$C_{12}$ alkyl (meth)acrylaide, an $NH_2$-substituted $C_2$-$C_{12}$ alkyl (meth)acrylamide, a methylamino-substituted $C_2$-$C_{12}$ alkyl (meth)acrylamide, a dimethylamino-substituted $C_2$-$C_{12}$ alkyl (meth)acrylamide, an ethylamino-substituted $C_2$-$C_{10}$ alkyl (meth)acrylamide, a diethylamino-substituted $C_2$-$C_8$ alkyl (meth)acrylamide, ethylene glycol (meth)acrylate, di(ethylene glycol) (meth) acrylate, tri(ethylene glycol) (meth)acrylate, tetra(ethylene glycol) (meth)acrylate, ethylene glycol methyl ether (meth) acrylate, di(ethylene glycol) methyl ether (meth)acrylate, tri(ethylene glycol) methyl ether (meth)acrylate, tetra(ethylene glycol) methyl ether (meth)acrylate, and combinations thereof.

7. The hydrogel ocular insert of claim 6, wherein the phosphorylcholine-containing vinylic monomer is selected from the group consisting of (meth)acryloylox-yethyl phosphorylcholine, (meth)acryloyloxypropyl phosphorylcholine, 4-((meth)acryloyloxy)butyl-2'-(trimethylammonio)ethylphosphate, 2-[(meth)acryloylamino]ethyl-2'-(trimethylammonio)-ethylphosphate, 3-[(meth)acryloylamino]propyl-2'-(trimethylammonio)ethylphosphate, 4-[(meth)acryloylamino]butyl-2'-(trimethylammonio) ethylphosphate, 5-((meth)acryloyloxy)pentyl-2'-(trimethylammonio)ethyl phosphate, 6-((meth)acryloyloxy)hexyl-2'-(trimethylammonio)-ethylphosphate, 2-((meth)acryloyloxy) ethyl-2'-(triethylammonio)ethylphosphate, 2-((meth)acryloyloxy)ethyl-2'-(tripropylammonio)ethylphosphate, 2-((meth)acryloyloxy)ethyl-2'-(tributylammonio)ethyl phosphate, 2-((meth)acryloyloxy)propyl-2'-(trimethylammonio)-ethylphosphate, 2-((meth)acryloyloxy)butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethyl phosphate, 2-(vinyloxy)ethyl-2'-(trimethylammonio)ethyl-phosphate, 2-(allyloxy)ethyl-2'-(trimethylammonio)ethylphosphate, 2-(vinyloxycarbonyl) ethyl-2'-(trimethylammonio)ethyl phosphate, 2-(allyloxycarbonyl)ethyl-2'-(trimethylammonio)ethylphosphate, 2-(vinylcarbonylamino)ethyl-2'-(trimethylammonio) ethylphosphate, 2-(allyloxycarbonylamino)ethyl-2'-(trimethylammonio)ethyl phosphate, 2-(butenoyloxy)ethyl-2'-(trimethylammonio)ethylphosphate, and combinations thereof.

8. The hydrogel ocular insert of claim 5, wherein said at least one acrylic monomer is n-butyl (meth)acrylate and/or di(ethylene glycol) methyl ether (meth)acrylate.

9. The hydrogel ocular insert of claim 8, wherein the phosphorylcholine-containing vinylic monomer is selected from the group consisting of (meth)acryloylox-yethyl phosphorylcholine, (meth)acryloyloxypropyl phosphorylcholine, 4-((meth)acryloyloxy)butyl-2'-(trimethylammonio)ethylphosphate, 2-[(meth)acryloylamino]ethyl-2'-(trimethylammonio)-ethylphosphate, 3-[(meth)acryloylamino]propyl-2'-(trimethylammonio)ethylphosphate, 4-[(meth)acryloylamino]butyl-2'-(trimethylammonio) ethylphosphate, 5-((meth)acryloyloxy)pentyl-2'-(trimethylammonio)ethyl phosphate, 6-((meth)acryloyloxy)hexyl-2'-(trimethylammonio)-ethylphosphate, 2-((meth)acryloyloxy)ethyl-2'-(triethylammonio)ethylphosphate, 2-((meth)acryloyloxy)ethyl-2'-(tripropylammonio)ethylphosphate, 2-((meth)acryloyloxy)ethyl-2'-(tributylammonio)ethyl phosphate, 2-((meth)acryloyloxy)propyl-2'-(trimethylammonio)-ethylphosphate, 2-((meth)acryloyloxy)butyl-2'-(trimethylammonio)ethylphosphate, 2-((meth)acryloyloxy)pentyl-2'-(trimethylammonio)ethylphosphate, 2-((meth)acryloyloxy)hexyl-2'-(trimethylammonio)ethyl phosphate, 2-(vinyloxy)ethyl-2'-(trimethylammonio)ethyl-phosphate, 2-(allyloxy)ethyl-2'-(trimethylammonio)ethylphosphate, 2-(vinyloxycarbonyl) ethyl-2'-(trimethylammonio)ethyl phosphate, 2-(allyloxycarbonyl)ethyl-2'-(trimethylammonio)ethylphosphate, 2-(vinylcarbonylamino)ethyl-2'-(trimethylammonio) ethylphosphate, 2-(allyloxycarbonylamino)ethyl-2'-(trimethylammonio)ethyl phosphate, 2-(butenoyloxy)ethyl-2'-(trimethylammonio)ethylphosphate, and combinations thereof.

10. The hydrogel ocular insert of claim 1, wherein the arylborono-containing hydrophilic copolymer comprises (a) from about 0.1% by mole to about 25% by mole of the arylborono-containing repeating units and (b) from about 75% by mole to about 99.9% by mole of repeating units of at least one hydrophilic vinylic monomer, provided that the sum of the mole percentages of components (a) and (b) and other components not listed above is 100%.

11. The hydrogel ocular insert of claim 1, wherein the arylborono groups independent of one another have a pKa of from about 7.2 to about 9.0, wherein said at least one arylborono-containing hydrophilic copolymer has a number average molecular weight of from about 5,000 Daltons to 500,000 Daltons.

12. The hydrogel ocular insert of claim 11, wherein said at least one mucoadhesive polymer comprises a galactomannan polymer, dextran, mannan, hyaluronic acid, polyvinyl alcohol.

13. The hydrogel ocular insert of claim 12, wherein said at least one mucoadhesive polymer comprises a guar and/or a chemically-modified galactomannan selected from the group consisting of Hydroxyethyl guar, hydroxypropyl guar, methyl guar, ethyl guar, propyl guar, carboxymethyl guar, carboxymethylhydroxypropyl guar, hydroxypropyltrimonium chloride guar, and combinations thereof.

14. The hydrogel ocular insert of claim 13, wherein said at least one mucoadhesive polymer is present in an amount of from about 50% to about 99% by weight relative to the dry weight of the hydrogel ocular insert.

15. The hydrogel ocular insert of claim 14, wherein the hydrogel ocular insert is hydrolytically stable in an aqueous solution at a pH of from about 7.5 to 9.5 and has an equilibrium water content of from about 10% to about 70% by weight (at room temperature, about 22° C. to 28° C.), when being fully hydrated.

16. The hydrogel ocular insert of claim 15, wherein the hydrogel ocular insert has a shape having a maximum size in any single dimension of 5-6 mm, wherein the hydrogel ocular insert has a shape of a rod, a sphere, an oval, a ring, a square, a rectangle, a triangle, or an irregular shape, wherein the hydrogel ocular insert has a thickness of about 50 to about 400 μm.

17. The hydrogel ocular insert of claim 16, wherein the packaging aqueous solution has a tonicity of from about 200 to about 450 milliosmol (mOsm).

18. The hydrogel ocular insert of claim 1, wherein said at least one mucoadhesive polymer is present in an amount of from about 50% to about 99% by weight relative to the dry weight of the hydrogel ocular insert.

19. The hydrogel ocular insert of claim 1, wherein the hydrogel ocular insert is hydrolytically stable in an aqueous solution at a pH of from about 7.5 to 9.5 and has an equilibrium water content of from about 10% to about 70% by weight (at room temperature, about 22° C. to 28° C.), when being fully hydrated.

20. The hydrogel ocular insert of claim 1, wherein the hydrogel ocular insert has a shape having a maximum size in any single dimension of 5-6 mm, wherein the hydrogel ocular insert has a shape of a rod, a sphere, an oval, a ring, a square, a rectangle, a triangle, or an irregular shape, wherein the hydrogel ocular insert has a thickness of about 50 to about 400 μm.

21. The hydrogel ocular insert of claim 1, wherein the hydrogel ocular insert has an on-eye dissolution time of at least 3 hours.

22. The hydrogel ocular insert of claim 1, wherein the hydrogel ocular insert has a layered structure and comprises a first hydrogel layer sandwiched between two second hydrogel layers, wherein the first hydrogel layer has a first crosslinking density of first crosslinks and the second hydrogel layers have a second crosslinking density of second crosslinks, wherein the first crosslinking density hydrolyze more slowly than the second crosslinks in the tear of the eye.

23. The hydrogel ocular insert of claim 12, wherein the hydrogel ocular insert comprises one or more additional pharmaceutical active agents.

24. The hydrogel ocular insert of claim 23, wherein said one or more additional pharmaceutical active agents are selected from the group consisting of ocular lubricants, anti-redness relievers, cooling agents, steroids and non-steroidal anti-inflammatory agents to relieve ocular pain and inflammation, antibiotics, anti-histamines, anti-virals, antibiotics and anti-bacterials for infectious conjunctivitis, anti-muscarinics for myopia treatment, and glaucoma drug delivery, and therapeutically suitable combinations thereof.

25. The hydrogel ocular insert of claim 24, wherein the packaging aqueous solution has a tonicity of from about 200 to about 450 milliosmol (mOsm).

* * * * *